US011369617B2

(12) United States Patent
Tiberg et al.

(10) Patent No.: US 11,369,617 B2
(45) Date of Patent: Jun. 28, 2022

(54) PROSTACYCLIN ANALOGUE FORMULATIONS

(71) Applicant: CAMURUS AB, Lund (SE)

(72) Inventors: Fredrik Tiberg, Lund (SE); Justas Barauskas, Lund (SE); Catalin Nistor, Lund (SE); Markus Johnsson, Lund (SE)

(73) Assignee: CAMURUS AB, Lund (SE)

( * ) Notice: Subject to any disclaimer, the term of this patent is extended or adjusted under 35 U.S.C. 154(b) by 104 days.

(21) Appl. No.: 16/333,448

(22) PCT Filed: Sep. 15, 2017

(86) PCT No.: PCT/EP2017/073359
§ 371 (c)(1),
(2) Date: Mar. 14, 2019

(87) PCT Pub. No.: WO2018/050864
PCT Pub. Date: Mar. 22, 2018

(65) Prior Publication Data
US 2019/0255068 A1   Aug. 22, 2019

(30) Foreign Application Priority Data
Sep. 15, 2016  (GB) ...................... 1615754
Dec. 14, 2016  (GB) ...................... 1621277

(51) Int. Cl.
*A61K 31/5585* (2006.01)
*A61P 9/10* (2006.01)
(Continued)

(52) U.S. Cl.
CPC ........ *A61K 31/5585* (2013.01); *A61K 9/0014* (2013.01); *A61K 9/0019* (2013.01);
(Continued)

(58) Field of Classification Search
CPC ..... A61K 31/5585; A61K 9/0014; A61P 9/10; A61P 9/12
See application file for complete search history.

(56) References Cited

U.S. PATENT DOCUMENTS 9,394,227 B1   7/2016 Zhang et al.
2006/0147520 A1* 7/2006 Ruegg ................. A61K 9/1617
424/464
2015/0328232 A1  11/2015 Malinin et al.

FOREIGN PATENT DOCUMENTS

CA   2113443 A1    2/1993
EP   2792353 A2 * 10/2014 ................ A61P 9/08
(Continued)

OTHER PUBLICATIONS

Search Report in GB Application No. GB1615754.7, dated Jun. 7, 2017.
(Continued)

*Primary Examiner* — San Ming R Hui
(74) *Attorney, Agent, or Firm* — J.A. Lindeman & Co. PLLC

(57) ABSTRACT

The present invention relates to an injectable pre-formulation comprising: a) at least one of a mono-, di-, or tri-acyl lipid and/or a tocopherol; b) optionally at least one phospholipid; c) at least one biocompatible, organic solvent; and d) at least one prostacyclin analogue or a salt thereof; wherein the pre-formulation forms, or is capable of forming, at least one liquid crystalline phase structure upon contact with excess aqueous fluid. Such compositions may additionally comprise polar co-solvents. Methods of treatment, particularly for management of pulmonary artery hypertension (PAH), severe PAH, Raynard's disease, ischemia and related conditions are provided, as well as corresponding uses of the
(Continued)

Figure 1A:
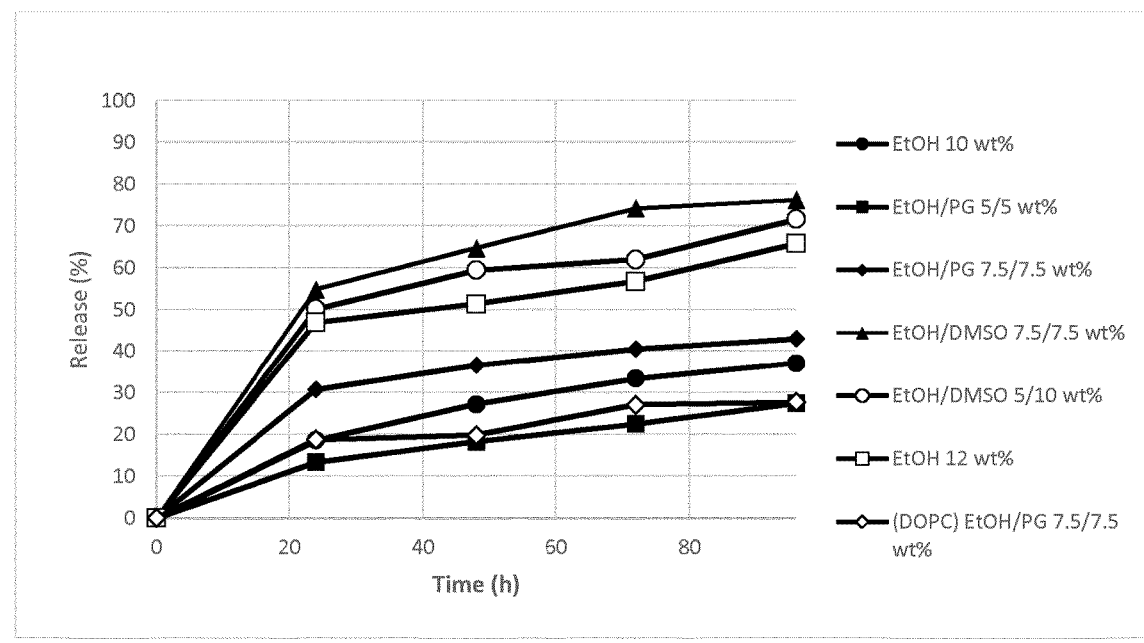

compositions. Administration devices comprising the formulations and kits comprising the devices are also provided.

31 Claims, 8 Drawing Sheets

(51) Int. Cl.
*A61P 9/12* (2006.01)
*A61K 9/00* (2006.01)
*A61K 31/192* (2006.01)
*A61K 31/5575* (2006.01)
*A61K 47/10* (2017.01)
*A61K 47/18* (2017.01)
*A61K 47/20* (2006.01)
*A61K 47/24* (2006.01)
*A61K 45/06* (2006.01)
*A61K 47/14* (2017.01)

(52) U.S. Cl.
CPC .......... *A61K 9/0024* (2013.01); *A61K 9/0053* (2013.01); *A61K 31/192* (2013.01); *A61K 31/5575* (2013.01); *A61K 45/06* (2013.01); *A61K 47/10* (2013.01); *A61K 47/14* (2013.01); *A61K 47/18* (2013.01); *A61K 47/20* (2013.01); *A61K 47/24* (2013.01); *A61P 9/10* (2018.01); *A61P 9/12* (2018.01)

(56) References Cited

FOREIGN PATENT DOCUMENTS

| RU | 2352323 C2 | 4/2009 | |
|---|---|---|---|
| WO | 93/02681 A1 | 2/1993 | |
| WO | 95/03787 A1 | 2/1995 | |
| WO | 03/101424 A1 | 12/2003 | |
| WO | 2005/117830 A1 | 12/2005 | |
| WO | 2006075125 A1 | 7/2006 | |
| WO | 2006/131730 A1 | 12/2006 | |
| WO | 2012/160213 A1 | 11/2012 | |
| WO | 2013024051 A1 | 2/2013 | |
| WO | 2013024052 A1 | 2/2013 | |
| WO | 2013/038460 A1 | 3/2013 | |
| WO | 2013/083459 A1 | 6/2013 | |
| WO | WO-2013083460 A1 * | 6/2013 | ............. A61K 38/08 |
| WO | 2014/085813 A1 | 6/2014 | |
| WO | 2014104788 A1 | 7/2014 | |
| WO | 2015/138423 A1 | 9/2015 | |
| WO | 2016/066655 A1 | 5/2016 | |

OTHER PUBLICATIONS

International Search Report and Written Opinion in International Application No. PCT/EP2017/073359, dated Dec. 5, 2017.
Product Pipeline Transcon Treprostinil, http://ascendispharma.com/product-pipeline/transcon-growth; accessed on Apr. 4, 2016.
Flolan prescribing information, Revised Apr. 2015.
Flolan Product Monograph, GlaxoSmithKline, Control No. 180478, Jul. 14, 2015.
Remodulin prescribing information, Revised Dec. 2014.
Ki et al., "A new injectable liquid crystal system for one month delivery of leuprolide", Journal of Controlled Release, 2014, 185: 62-70.
Obata et al., "Single Injection of a Sustained-release Prostacyclin Analog Improves Pulmonary Hypertension in Rats", American Journal of Respiratory and Critical Care Medicine, vol. 177, 2008, pp. 195-201.
Yaghmur et al., "In situ forming drug delivery systems based on lyotropic liquid crystalline phases: structural characterization and release properties", J. Drug Del. Sci. Tech., 23 (4), 2013; pp. 325-332.
D.A. Harkevich, Pharmacology, Moscow, publishing house "Medicine", 1987, pp. 47-48, English translation of relevant parts.
Dyson G. and May P., "Chemistry of synthetic drugs", Moscow, publishing house "The World", 1964, pp. 12-19,English translation of relevant parts.
V.G. Belikov "Pharmaceutical chemistry", textbook, 2007, Moscow, publishing house "MEDpress-inform", pp. 27-29, English translation of relevant parts.
"Guideline for Conducting Preclinical Trials of Drugs", Part 1, Moscow: publishing house Griph and K, 2012, 944 pages, edited by Mironov A.N., pp. 436, 441, 442.
Bajwa et al., "The safety and tolerability of inhaled treprostinil in patients with pulmonary hypertension and chronic obstructive pulmonary disease", Pulmonary Circulation, 7(1): 82-88 (2017).
Inzhutova, "Iloprost—an affordable prostacyclin for the treatment of pulmonary arterial hypertension",Consilium Medicum,14(10):93-97(2012).
Zhulenko et al., "Pharmacology", 34-35, KolosS (2008).

* cited by examiner

PROSTACYCLIN ANALOGUE FORMULATIONS

FIELD OF THE INVENTION

The present invention relates to formulation precursors (pre-formulations) for the in situ generation of compositions for the controlled release of active agents, and methods of treatment with such formulations. In particular, the invention relates to pre-formulations of amphiphilic components and at least one prostacyclin analogue, which undergo phase transition upon exposure to aqueous fluids, such as body fluids, thereby forming a controlled release composition.

BACKGROUND TO THE INVENTION

Many bioactive agents including pharmaceuticals, nutrients, vitamins and so forth have a "functional window". That is to say that there is a range of concentrations over which these agents can be observed to provide some biological effect. Where the concentration in the appropriate part of the body (e.g. locally or as demonstrated by serum concentration) falls below a certain level, no beneficial effect can be attributed to the agent. Similarly, there is generally an upper concentration level above which no further benefit is derived by increasing the concentration. In some cases increasing the concentration above a particular level results in undesirable or even dangerous effects.

Some bioactive agents have a long biological half-life and/or a wide functional window and thus may be administered occasionally, maintaining a functional biological concentration over a substantial period of time (e.g. 6 hours to several days). In other cases the rate of clearance is high and/or the functional window is narrow and thus to maintain a biological concentration within this window regular (or even continuous) doses of a small amount are required. This can be particularly difficult where non-oral routes of administration (e.g. parenteral administration) are desirable or necessary, since self-administration may be difficult and thus cause inconvenience and/or poor compliance. In such cases it would be advantageous for a single administration to provide active agent at a therapeutic level over the whole period during which activity is needed.

One particular class of active agents having a high rate of clearance and short half-life are prostacyclin and its analogues. Prostacyclin is an endogenous member of the eicosanoid family and is involved in several processes including platelet activation, vasodilation and blood pressure regulation. Prostacyclin is also known as epoprostenol when referring to synthetically derived material, and the terms are used interchangeably herein.

Epoprostenol was approved for the treatment of pulmonary arterial hypertension (PAH) by the FDA in 1995. PAH is potentially fatal condition characterized by a mean pulmonary artery pressure (mPAP) of ≥25 mmHg, with normal pulmonary artery wedge pressure (PAWP) (≤15 mmHg). However, as epoprostenol itself has an in vivo half-life of less than one minute, it requires continual administration, typically through a central venous catheter. Epoprostenol sodium for intravenous therapy is marketed as Flolan® (GlaxoSmithKline). Since 2008 a room-temperature stable formulation of epoprostenol (Veletri®, Actelion Pharmaceuticals) has also been available. An estimated 100,000 to 200,000 individuals are believed to be affected by PAH worldwide.

Several prostacyclin analogues with longer half-lives are known, including iloprost (Bayer), and treprostinil. Treprostinil was approved by the FDA in 2002 and has a plasma half-life of 2.9 to 4.6 hours. Despite the longer half-life compared with epoprostenol, continual i.v. infusion or regular s.c. administration of treprostinil is still generally necessary. IV therapy requires surgical insertion of a central venous catheter, carries the risk of infection and thrombosis and is naturally uncomfortable for the patient. Epoprostenol can also be administered through inhalation or oral routes. However, these routes provide a lower cumulative dose of epoprostenol than the IV route. They may thus not be suitable for all patients.

Remodulin® (United Therapeutics Corporation) is a formulation of treprostinil designed for IV or continuous s.c. injection. Continuous s.c. injection is achieved by means of a microinfusion pump. Although this addresses some of the issues associated with bulky pump equipment, it is still not ideal and furthermore it is recommended that patients have immediate access to a backup infusion pump.

Although regular s.c. administration somewhat addresses the disadvantages of i.v. or continuous s.c. administration, oral or inhalation routes, administration-site pain is a significant obstacle in the majority of patients (experienced by 85% of patients) and is responsible for almost all withdrawals from treprostinil due to adverse events (a total of 23% of the long-term study population). This has hereto been managed, to the extent possible, by appropriate site selection. Site pain peaks in the first few days after a site change, and use of a single site for 4 weeks or more can be helpful and safe in some cases.

There is an evident need for a preparation of prostacyclin analogue(s) which is stable to storage, which can be administered without the need for continuous administration though a central venous catheter or by continuous s.c. administration, which is not susceptible to the risk of mechanical failure and/or which can be administered less frequently whilst causing less site pain than existing s.c. formulations. The present invention addresses some or all of these deficiencies.

Patients undergoing treatment for PAH typically require a therapeutic dose to be maintained for a considerable period and typically require ongoing treatment for many months or years. Thus a depot system allowing loading and controlled release of a larger dose over a longer period would offer a considerable advantage over conventional delivery systems.

In this regard, polymer delivery systems containing treprostinil have been developed, such as TransCon Treprostinil (Ascendis Pharma) which has undergone Phase 1 clinical trials. TransCon Treprostinil is designed as a once-daily self-administered s.c. injection of treprostinil and is based on a polymer delivery system, especially a poly (oxazoline) or PEG-based polymer. TransCon Treprostinil is intended to offer the same efficacy as continuously-infused prostacyclin analogues, but with a safer and more convenient route of administration with reduce site reaction and bloodstream infection risks associated with current parenteral administration routes.

The poly-lactate, poly-glycolate and poly-lactate-co-glycolate polymers typically used for degrading slow-release formulations are also the cause of some irritation in at least some patients. In particular, these polymers typically contain a certain proportion of acidic impurities such as lactic and glycolic acid, which will irritate the injection site on administration. When the polymer then breaks down, lactic acid and glycolic acid are the degradation products so that further irritation is caused.

Despite the potential advantages offered by TransCon Treprostinil in terms of patient comfort and somewhat less frequent (once daily) administration, even if a polymer such as a PEG is used which is not broken down into acidic impurities, polymer systems tend to be of high viscosity and consequently require injection through a wide needle and/or provide only a fairly short duration product. PEG-grafting to an active agent such as treprostinil typically increases the biological lifetime but may interfere with binding and cannot currently provide a product that will remain active for several days between injection. As a result of the combined effects of wide-needle administration and/or irritant contents, discomfort at the site of administration and the formation of connective scar tissue are often greater than desirable. This is increased in the case of the proposed Treprostinil formulation since injection is at least daily, rather than weekly or longer periodicity. As a result, over a long treatment duration, either multiple irritant administrations must be made at a small number of sites, or a large number of sites utilised, with resultant widespread discomfort for the subject.

Evidently, it would be an advantage to provide a system of low viscosity, such as a homogeneous solution, dispersion of fine particles, or $L_2$ phase, which could be administered easily through a narrow needle, thus decreasing the discomfort of the patient during the procedure and causing less site pain. This ease of administration is particularly significant where patients will be on a self-administration regime and may already be self-administering several times each day, as is the case with several existing treprostinil treatments. Providing a sustained formulation with a duration of a few days, but which is sufficiently complex to administer that it requires treatment by a healthcare professional will not be an advantage to all patients over twice-daily or daily self-administration, and is likely to be more costly. Providing a formulation which gives sufficiently long duration to justify a visit to a health professional for administration and/or a preparation which can be self-administered easily would be a significant advantage. Reducing preparation time of health-care professionals or patients prior to the actual administration is also an important issue.

From a drug delivery point of view, polymer depot compositions also generally have the disadvantage of accepting only relatively low drug loads and having a "burst/lag" release profile. The nature of the polymeric matrix, especially when applied as a solution or pre-polymer, causes an initial burst of drug release when the composition is first administered. This is followed by a period of low release, while the degradation of the matrix begins, followed finally by an increase in the release rate to the desired sustained profile. This burst/lag release profile can cause the in vivo concentration of active agent to burst above the functional window immediately following administration, and then drop back through the bottom of the functional window during the lag period before reaching a sustained functional concentration for a period of time. Evidently, from a functional and toxicological point of view this burst/lag release profile is undesirable and could be dangerous. It may also limit the equilibrium concentration which can be provided due to the danger of adverse effects at the "peak" point. The presence of a lag phase may furthermore require supplementary dosing with repeat injections during the start-up period of depot treatment in order to maintain a therapeutic dose while the concentrations of active provided from the depot are sub-functional.

Controlled-release formulations are typically generated from bio-compatible polymers in the form of, for example, implants or injectable beads. Polymer microsphere formulations must generally be administered by means of a sizable needle, typically of 20-gauge or wider. This is necessary as a result of the nature of the polymeric dosing systems used, which are typically polymer suspensions. It would be an advantage to provide a system of low viscosity, such as a homogeneous solution, dispersion of fine particles, or $L_2$ phase, which could be administered easily through a narrow needle, thus decreasing the discomfort of the patient during the procedure. Ease of administration is particularly significant when patients will be self-administering but also reduces the burden on healthcare professionals when they are conducting the administration.

The manufacture of PLGA microbeads and suspensions is additionally a considerable difficulty with certain existing depot systems. In particular, since the beads are particulate they cannot generally be sterile-filtered and furthermore, since the PLGA copolymer melts at elevated temperature, they cannot be heat-treated for sterility. As a result, the complex manufacturing process must be conducted aseptically.

Further issues with biodegradable polymer microspheres include complex reconstitution prior to injection and limited storage stability, due both to aggregation and degradation of the delivery system and/or active.

A lipid-based, slow-release composition has been described for certain peptides. For example, WO2006/131730 discloses a lipid depot system for GLP-1 and analogues thereof. This is a highly effective formulation, but the concentration of active agent which can be included in the formulation is limited by its solubility. Evidently, a higher concentration of active agent allows for the possibility of longer duration depot products, products maintaining a higher systemic concentration, and products having a smaller injection volume, all of which factors are of considerable advantage under appropriate circumstances. It would thus be of considerable value to establish a way by which higher concentrations of active agents could be included in a lipid-based depot formulation and to identify combinations of active agent and delivery system which are particularly effective from the point of view of loading, stability, manufacturing and/or controlled release.

The present inventors have now established that by providing a pre-formulation comprising at least one neutral mono-, di- or triacyl lipid and/or a tocopherol, optionally at least one phospholipid, at least one biocompatible organic mono-alcoholic solvent, and at least one prostacyclin analogue or a salt thereof in a low viscosity phase, such as molecular solution or $L_2$ (reversed micellar) phase, a pre-formulation may be generated addressing many of the shortfalls of known treprostinil formulations, and which may be applied to provide a controlled release of the prostacyclin analogue. By use of specific components in carefully selected ratios, a depot formulation can be generated having a combination of properties exceeding the performance of existing prostacyclin analogue formulations, and providing an advantage over known treprostinil compositions such as Remodulin® or TransCon treprostinil.

In particular, the pre-formulation shows a highly advantageous release profile, is easy to manufacture, may be sterile-filtered, has low viscosity (allowing easy and less painful administration typically through a narrow needle), allows a high level of bioactive agent to be incorporated (thus potentially allowing a smaller amount of composition and/or active agent to be used), requires shallow injection and/or forms a desired non-lamellar depot composition in vivo having a "low-burst" release profile. The compositions are also formed from materials that are non-toxic, biotolerable and biodegradable, which can be administered by single i.m., or s.c. injection rather than central venous catheter or continuous s.c. injection, and are suitable for self-administration. The pre-formulation may additionally have a very low level of irritation on injection and in preferred cases causes no irritation at the injection site (including transient irritation). The pre-formulations may be administered less frequently than even proposed "slow release" formulations, resulting in better compliance from the patient and/or less irritation due to repeated frequent administrations.

Formulations of the present invention generate a non-lamellar liquid crystalline phase following administration. The use of non-lamellar phase structures (such as non-lamellar liquid crystalline phases) in the delivery of bioactive agents is now relatively well established. A most effective lipid depot system is described in WO2005/117830, and a highly preferred lipid depot is described in that document. However, there remains scope for achieving depot formulations having improved performance in several respects and in particular, surprising improvements can be achieved by careful selection and optimisation of the range of components and proportions disclosed in previous work.

Advantages of the compositions of the present invention over polymer formulations, such as PLGA microspheres, include the ease of manufacture (including sterilization), handling and use properties combined with low initial release ("low-burst profile") of active agent. This may be defined such that the area under a plasma concentration against time the curve during the first 24 hours of a one-week dosing period is less than 50% of the area under the curve for the entire curve (measured or extrapolated from time 0 to infinity or from time 0 to the last sampling time point), more preferably less than 40% and most preferable less than 30%. Furthermore, it may be defined such that the maximum plasma concentration of active agent in vivo following injection of the pre-formulation (Cmax) is no more than 10 times, preferably no more than 8 times and most preferably no more than 5 times the average plasma concentration during the therapeutic period (Cave) (i.e. Cmax/Cave≤10, preferably ≤8, more preferably ≤5).

SUMMARY OF THE INVENTION

The present invention provides a pharmaceutical formulation comprising an appropriate combination of lipid excipients, organic alcoholic solvent and prostacyclin analogue and certain optional components, that can be used as a depot-precursor formulation (referred to herein for brevity as a pre-formulation) to address one or more of the needs described above. The inventors have established that by optimising these components, depot compositions of a prostacyclin analogue, especially treprostinil, and corresponding precursor formulations with a highly advantageous combination of properties can be generated.

In a first embodiment the invention provides a pre-formulation comprising:
  a) at least one of a mono-, di- or tri-acyl lipid and/or a tocopherol;
  b) optionally at least one phospholipid;
  c) at least one biocompatible, organic solvent; and
  d) at least one prostacyclin analogue or a salt thereof;
wherein the pre-formulation optionally but preferably forms, or is capable of forming, at least one liquid crystalline phase structure upon contact with excess aqueous fluid.

In a preferred embodiment applicable to all aspects of the invention the prostacyclin analogue contains a 3,4-cis fused cyclopentane ring, an OH group at the 1-position of said cyclopentane ring and a C1-10 group at the 2-position of the cyclopentane ring, these structures being defined in more detail herein. The prostacyclin analogue may, for example, be of formula I, Ia, Ib or Ic as indicated herein.

Prostacyclin analogues according to the invention will typically include a carboxylic acid moiety within the molecule or may be salts thereof. However, where the prostacylin analogue does not contain an acid unit and is not capable of forming a salt, the term "free acid" as used herein is to be interpreted as neutral molecule (e.g. neutral ester).

In another preferred embodiment the prostacyclin analogue (free acid) has a molecular weight of less than 500 g/mol and is not a polypeptide.

In another preferred embodiment the prostacyclin analogue (free acid) is present at a level of 0.1 to 10% of the pre-formulation, preferably 0.2 to 6% In an embodiment the prostacyclin analogue (free acid) is present at a level such as 0.2 to 5%, 0.5 to 5%, especially 0.2 to 4% or 0.75 to 4%.

In another preferred embodiment the prostacyclin analogue comprises or consists of treprostinil (TPN) or a salt thereof, preferably treprostinil sodium salt.

In a preferred embodiment component c) comprises or consists of at least one solvent selected from the group consisting of: alcohols, amines, amides, sulphoxides and/or esters.

In a preferred embodiment c) comprises or consists of ethanol or mixtures of ethanol and propylene glycol, preferably wherein the ratio of ethanol to PG is 1:1 to 10:1, more preferably 1.5:1 to 8:1, most preferably 2:1 to 5:1 (e.g. around 3:1).

In another preferred embodiment the pre-formulation has a stability after 3 months of at least 96%, preferably at least 97%, especially at least 98% in terms of active agent assay as measured by HPLC, at 25° C. and 60% RH, preferably after 6 months, especially after 12 months, as defined herein.

In another preferred embodiment the pre-formulation has a stability after 1 month of at least 96%, preferably at least 97%, especially at least 98%, in terms of active agent assay as measured by HPLC following storage at 40° C. and 75% RH, after preferably after 3 months, especially after 6 months.

In an especially preferred embodiment
  component a) comprises or consists of GDO,
  component b) comprises or consists of soy PC;
  component c) comprises ethanol and optionally propylene glycol; and
  component d) comprises or consists of treprostinil or a salt thereof (e.g. sodium).

In a second aspect the invention relates to the use a pre-formulation as defined herein in the sustained administration of a prostacyclin analogue.

In another aspect the invention provides a pre-formulation according to the first embodiment or a composition derived by exposing said pre-formulation to excess aqueous fluid, for use as a medicament (e.g. for use in the treatment of the conditions described herein).

In another aspect the invention provides a method for the treatment of a human or non-human mammalian subject comprising administering to said subject a pre-formulation as defined herein.

In one embodiment, the method of treatment (as well as corresponding uses and other aspects) is a method for the treatment of a human or non-human mammalian subject (especially one in need thereof). In a further embodiment, the method of treatment (as well as corresponding uses and other aspects) is a method for the treatment of at least one condition selected from pulmonary artery hypertension (PAH), PAH-associated chronic obstructive pulmonary disease (COPD), severe Raynaud's disease, ischemia and related conditions.

In an embodiment the method of treatment involves administration a pre-formulation as defined herein every 1 to 60 days, preferably every 1, 2, 3, 7, 14, 21, 28, 30, or 60 days (e.g. ±3 days, or 20% in any case), most preferably every 7 (±1) days or every 14 (±2) days, or every 30 (±3) days.

In an embodiment the method of treatment involves administering said prostacyclin analogue or salt thereof at a level of 0.005 to 2.5 mg/kg/week, preferably at a level of 0.01 to 1 mg/kg/week, especially 0.015 to 0.7 mg/kg/week.

In another aspect the invention relates to a pre-formulation as described herein for use in a method of treatment as described herein (including all diseases, conditions, dosages, methods or administration and administration protocols described herein).

In another aspect the invention relates to the use of a pre-formulation as defined herein in the manufacture of a medicament for use in the in vivo formation of a depot for treatment of at least one condition selected from pulmonary artery hypertension (PAH), PAH-associated COPD, Raynaud's disease, ischemia and related conditions.

In another aspect the invention provides a pre-filled administration device containing a pre-formulation as defined herein.

In another aspect the invention relates to a kit comprising an administration device as defined herein, preferably including an auto-injector, cartridge and/or pen.

BRIEF SUMMARY OF THE ATTACHED FIGURES

FIG. 1. In vitro release profiles of selected formulations from Table 1 as a function of time (a) and square root of time (b).

Figure 2:
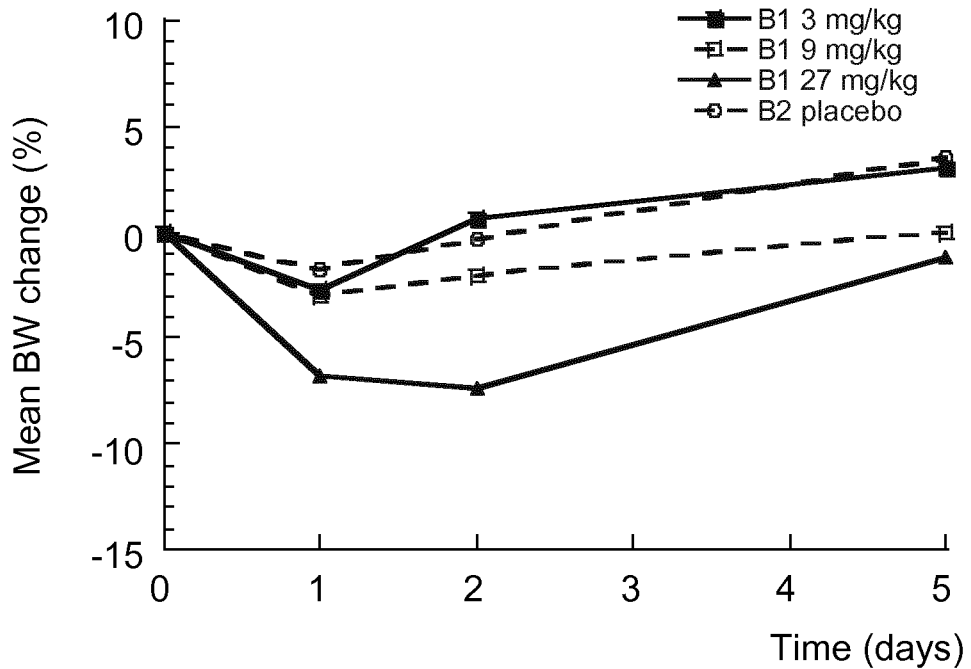

FIG. 2. Results of bodyweight change in rats during the pilot study dosing using formulations B1 and B2 (see Example 2 and Table 2).

Figure 3:
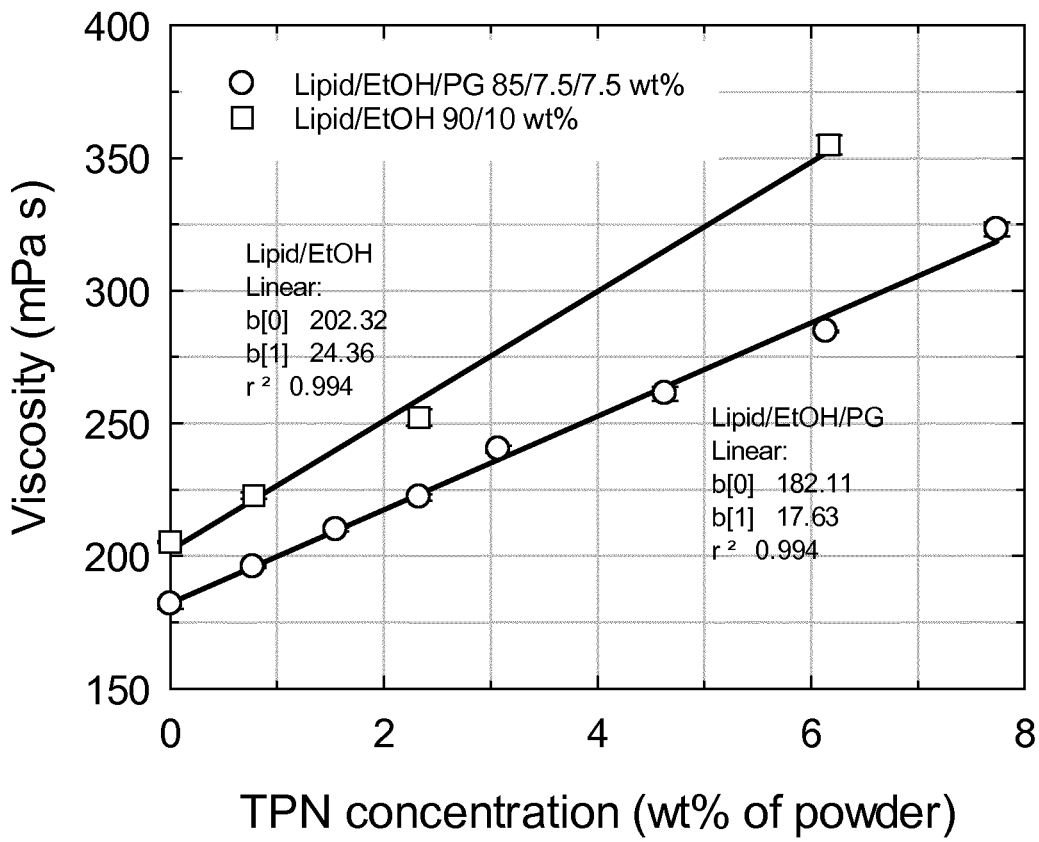

FIG. 3. Viscosity of selected formulations L-AA (see Example 3 and Table 6)

FIG. 4. In vitro release profiles of formulations N, P, Q, R and S (cumulative percentage release) (a) with the 0-20% release region in expanded view (b).

Figure 5:
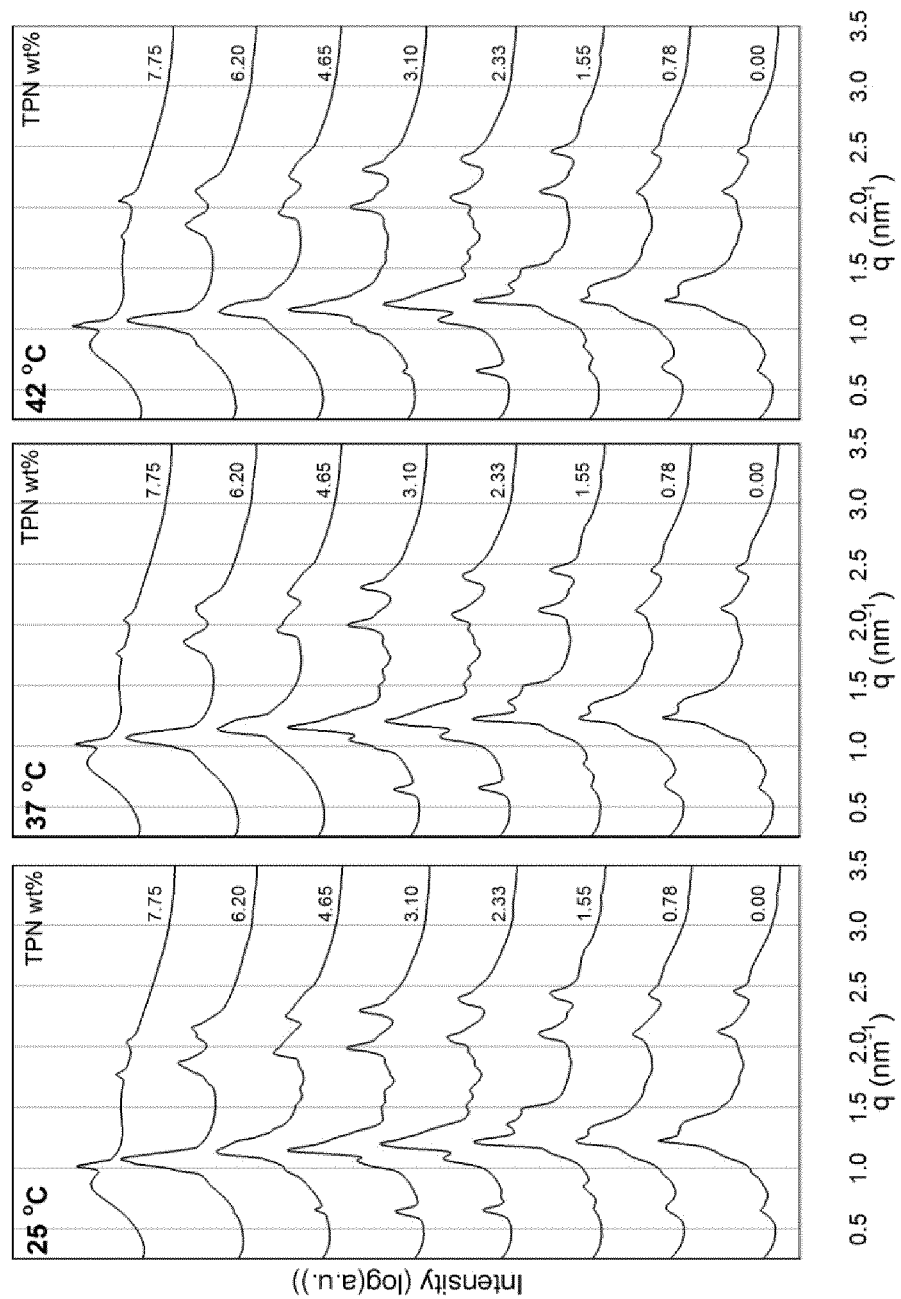

FIG. 5. X-ray diffractograms at 25° C., 37° C. and 42° C. of Formulations L-S after equilibration in aqueous medium.

Figure 6:
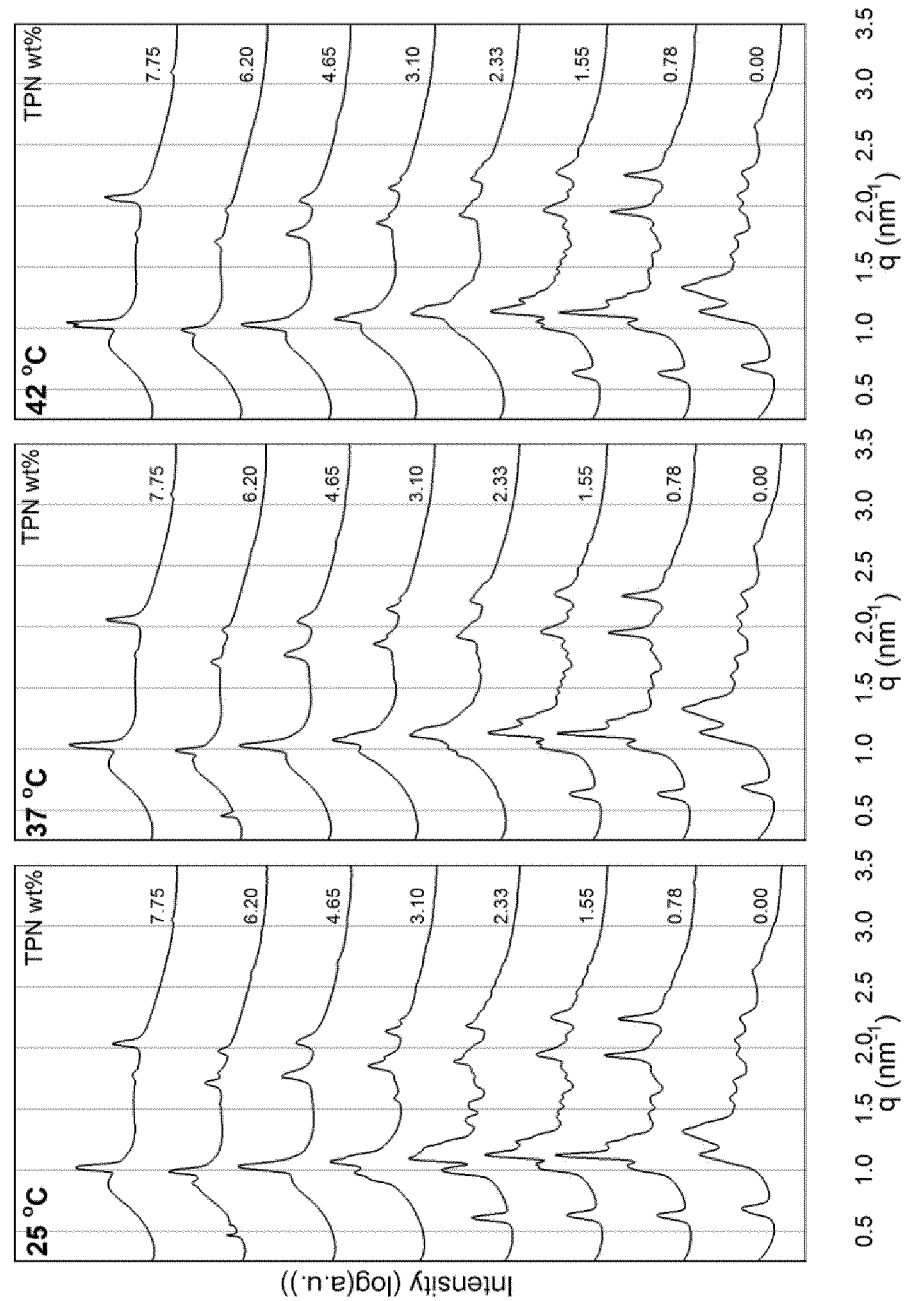

FIG. 6. X-ray diffractograms at 25° C., 37° C. and 42° C. of Formulations T-AA after equilibration in aqueous medium.

Figure 7:
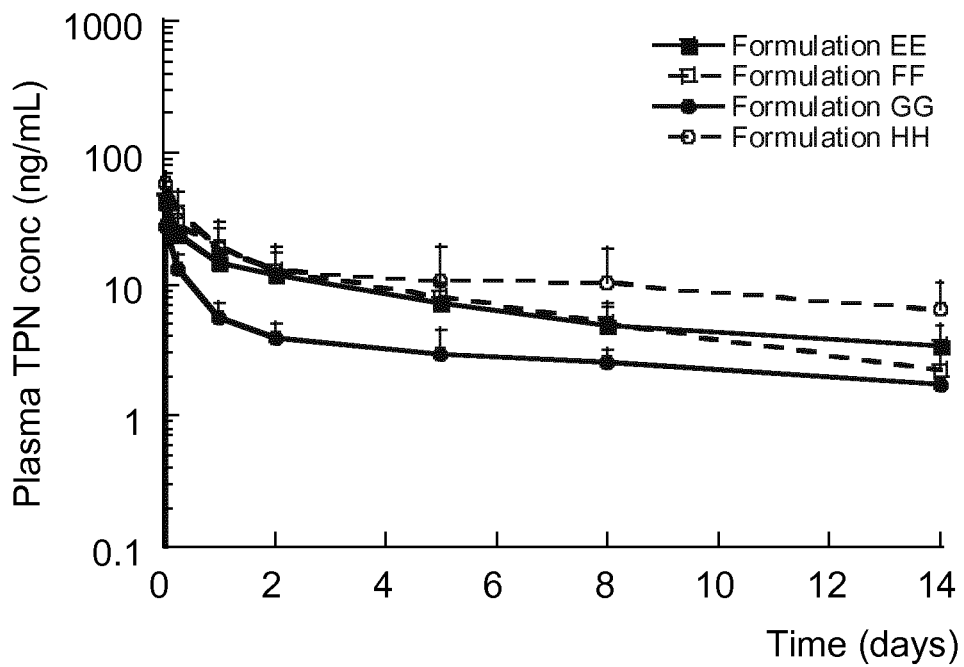

FIG. 7. Mean plasma concentrations of TPN in rats following administration of Formulations EE, FF, GG or HH.

Figure 8:
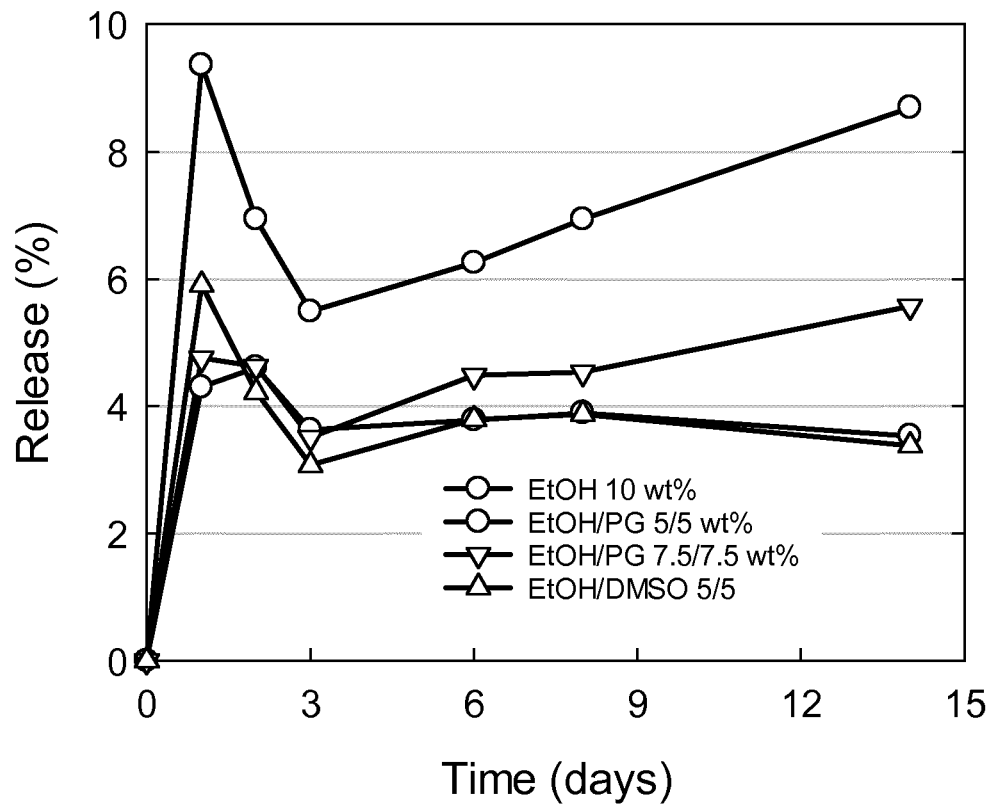

FIG. 8. In vitro release profiles (cumulative percentage release) of formulations FF, EE, X and HH.

Figure 9:
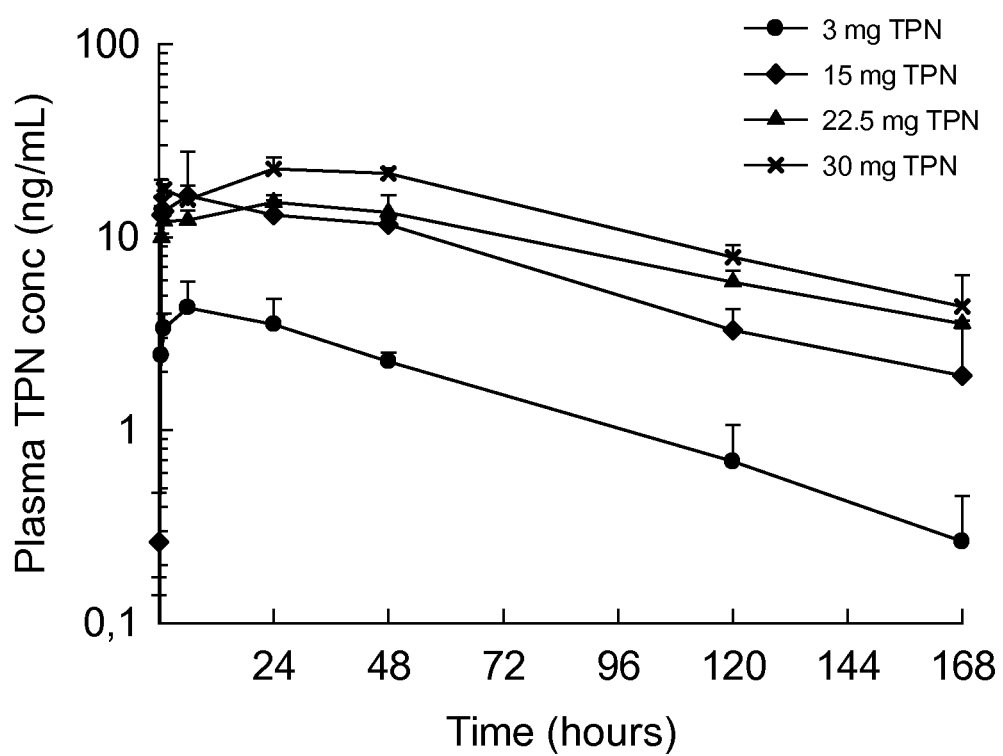

FIG. 9. Mean Treprostinil Plasma Concentration-Time Profiles Following a Single Subcutaneous Injection of 3, 15, 22.5 and 30 mg TPN in pre-formulation to a Male and Female Beagle Dogs.

Figure 10:
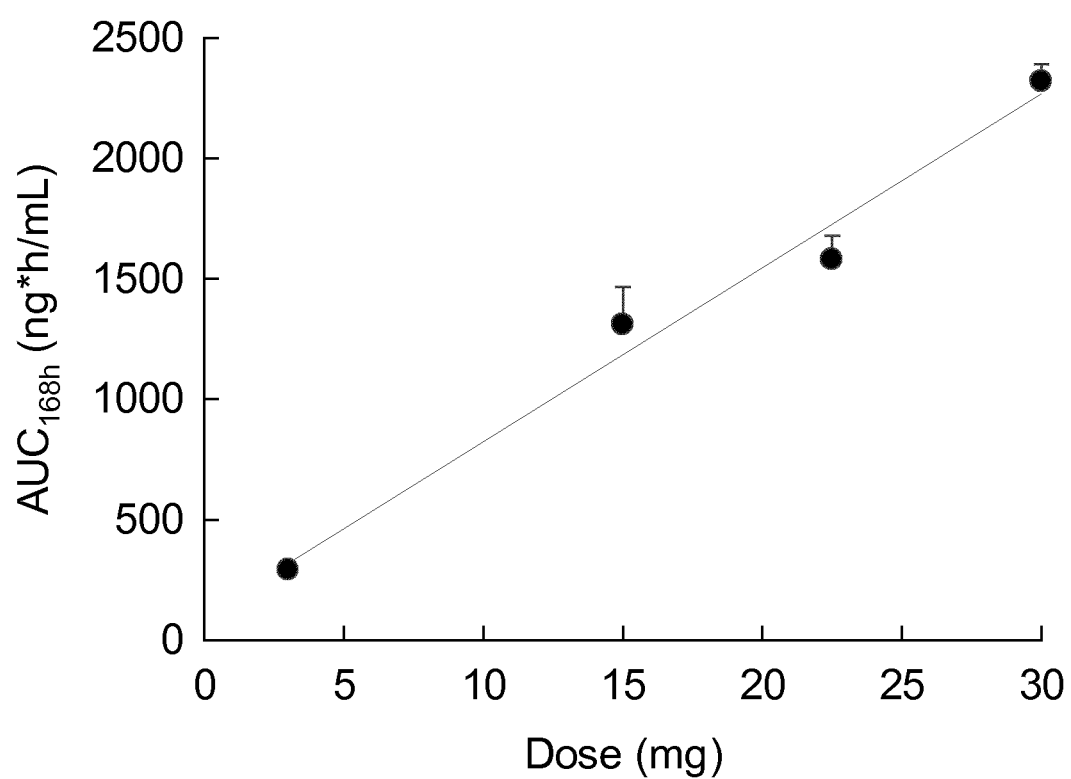

FIG. 10. Mean Treprostinil $AUC_{0-168\,hr}$ Values Following A Single Subcutaneous Injection of 3, 15, 22.5, and 30 mg TPN in pre-formulation to Male and Female Beagle Dogs.

DETAILED DESCRIPTION OF THE INVENTION

The formulations of the present invention generate a non-lamellar liquid crystalline phase following administration. The use of non-lamellar phase structures (such as liquid crystalline phases) in the delivery of bioactive agents is now relatively well established. A most effective lipid depot system for general use is described in WO2005/117830, and a suitable lipid matrix for use in the present invention is described in general terms in that document, the full disclosure of which is hereby incorporated herein by reference. For a description of the most favourable phase structures of such formulations, attention is drawn to the discussion in WO2005/117830 and particularly to page 29 thereof.

All % are specified by weight herein throughout, unless otherwise indicated. Furthermore, the % by weight indicated is the % of the total pre-formulation including all of the components indicated herein where context allows. Weight percentages of prostacyclin analogue will be calculated on the basis of the weight of free acid irrespective of whether the acid or a salt thereof is used. The pre-formulations can optionally consist of essentially only the components indicated herein (including where appropriate additional optional components indicated herein below and in the attached claims) and in one aspect consist entirely of such components. Where a formulation is indicated as "consisting essentially of" certain components herein, when the specified components provide the essential nature of that formulation, such as when the specified components constitute at least 95%, preferably at least 98%, of the formulation.

Preferably the pre-formulation according to the invention is a molecular solution or has an $L_2$ phase structure (prior to administration). The pre-formulation forms a non-lamellar (e.g. liquid crystalline) phase following administration. Such a phase change is typically brought about by absorption of aqueous fluid from the physiological environment, as indicated herein. Although it has previously been established in WO2012/160213 that a carefully controlled amount of water can be tolerated provided that a mono-alcoholic solvent is present, it will be understood that upon administration the pre-formulation is exposed to a large amount of aqueous fluid. Typically the pre-formulation will form a non-lamellar phase upon contact with at least an equivolume amount of aqueous fluid.

The present inventors have now surprisingly established that by appropriate choice of types, absolute amounts and ratios of lipid components along with a prostacyclin analogue and a biocompatible organic solvent, the release properties of the depot compositions formed from the pre-formulations of the invention can be rendered highly advantageous and superior to existing depot formulations of treprostinil. In particular, the release duration of a single administration of the prostacyclin analogue if far beyond that of existing treprostinil depots, with the maximum plasma concentration in vivo being only a small multiple of the average or even minimum concentration during the dosing period.

Component a)—Acyl Lipid/Tocopherol

Preferable ranges for component a) are 15-85 wt. %, preferably 20-80%, preferably 30-60 wt. %, preferably 35-55%, such as 38-52%, especially 38 to 52%. Levels of around 43% (e.g. 41 to 45%) are particularly preferred in some embodiments.

Preferable ranges for component b) are 15-85 wt. %, preferably 20-80%, preferably 30-60 wt. %, preferably 35-55%, such as 38-52%, especially 38 to 52%. Levels of around 43% (e.g. 41 to 45%) are particularly preferred in some embodiments.

Ratios of a:b are typically 40:60 to 60:40, preferably 45:55 to 55:45 and more preferably 47:53 to 53:47. Ratios of around 50:50 (e.g. ±2) are highly effective.

Component "a" as indicated herein comprises one or more of a mono- or di-acyl lipid and/or a tocopherol. Most preferably component a) comprises or consists of a mono- or diacyl lipid and thus has one or two non-polar "tail" groups. Acyl glycerols for use in the present invention (e.g. mono- or di-acyl glycerols) will generally not form a non-lamellar liquid crystalline phase structures as a pure compound in water at 25° C.

In one embodiment component a) may be a mono-acyl lipid. Mono-acyl lipids contain a polar "head" group and one non-polar "tail group". The "head" group may be glycerol, diglycerol, sugar moieties (such as inositol and glucosyl based moieties); and esters of polyols, such as acetate or succinate esters. A preferred class of mono-acyl lipids are esters of hexitans such as sorbitan. In this terminology "hexitan" denotes a hexitol of formula $HOCH_2(CHOH)_4CH_2OH$ which has cyclised by losing one equivalent of water to form a five or six membered ring, preferably a five membered furanose ring. Sorbitan is a particularly preferred head group. The head group is linked to the tail group preferably via an ester linkage. Suitable tail groups are discussed below.

In a particularly preferred embodiment component a) comprises or consists of at least one diacyl lipid, preferably a diacyl glycerol (DAG). A diacyl lipid comprises a polar head group as described above and two apolar tail groups, preferably linked to the polar head group via an ester linkage. The most preferred polar head group for diacyl lipids is glycerol.

The non-polar group(s) may have the same or a differing number of carbon atoms and may each independently be saturated or unsaturated. Examples of non-polar groups include $C_6$-$C_{32}$ alkyl and alkenyl groups, which are typically present as the esters of long chain carboxylic acids. These are often described by reference to the number of carbon atoms and the number of unsaturations in the carbon chain. Thus, CX:Z indicates a hydrocarbon chain having X carbon atoms and Z unsaturations. Examples particularly include lauroyl (C12:0), myristoyl (C14:0), palmitoyl (C16:0), phytanoyl (C16:0), palmitoleyl (C16:1), stearoyl (C18:0), iso-stearoyl (C18:0), oleoyl (C18:1), elaidoyl (C18:1), linoleoyl (C18:2), linolenoyl (C18:3), arachidonoyl (C20:4), behenoyl (C22:0) and lignoceroyl (C24:9) groups. Thus, typical non-polar chains are based on the fatty acids of natural ester lipids, including caproic, caprylic, capric, lauric, myristic, palmitic, phytanic, palmitolic, stearic, oleic, elaidic, linoleic, linolenic, arachidonic, behenic or lignoceric acids, or the corresponding alcohols. Preferable non-polar chains are palmitic, stearic, oleic and linoleic acids, particularly oleic acid.

Mixtures of any number of mono- or diacyl lipids may be used as component a). Preferably this component will include at least a portion of C18 lipids (e.g. DAG having one or more (i.e. one or two) C18:0, C18:1, C18:2 or C18:3 non-polar groups), such as sorbitan monooleate (SMO), glycerol dioleate (GDO) and/or glycerol dilinoleate (GDL). A highly preferred example is DAG comprising at least 50%, preferably at least 80% and even comprising substantially 100% GDO.

Since GDO and other mono- and di-acyl glycerols are products derived from natural sources, there is generally a certain proportion of "contaminant" lipid having other chain lengths etc. In one aspect, GDO as used herein is thus used to indicate any commercial grade of GDO with concomitant impurities (i.e. GDO of commercial purity). These impurities may be separated and removed by purification but providing the grade is consistent this is rarely necessary. If necessary, however, "GDO" may be essentially chemically pure GDO, such as at least 80% pure, preferably at least 85% pure and more preferably at least 90% pure GDO.

An alternative or additional preferred class of compounds for use as all or part of component a) are tocopherols. As used herein, the term "a tocopherol" is used to indicate the non-ionic lipid tocopherol, often known as vitamin E, and/or any suitable salts and/or analogues thereof. Suitable analogues will be those providing the phase-behaviour, lack of toxicity, and phase change upon exposure to aqueous fluids, which characterise the compositions of the present invention. Such analogues will generally not form a non-lamellar liquid crystalline phase structures as a pure compound in water at 25° C. The most preferred of the tocopherols is tocopherol itself, having the structure below. Evidently, particularly where this is purified from a natural source, there may be a small proportion of non-tocopherol "contaminant" but this will not be sufficient to alter the advantageous phase-behaviour or lack of toxicity. Typically, a tocopherol will contain no more than 10% of non-tocopherol-analogue compounds, preferably no more than 5% and most preferably no more than 2% by weight.

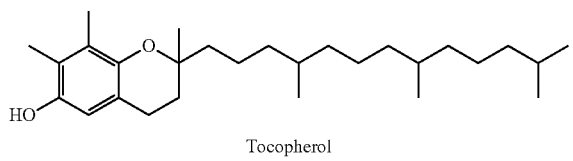 [SMILES: Cc1c(O)cc2c(c1C)OC(C)(CCCC(C)CCCC(C)CCCC(C)C)CC2]

Tocopherol

In one embodiment of the invention, component a) consists essentially of tocopherols, in particular tocopherol as shown above.

A preferred combination of constituents for component a) is a mixture of at least one diacyl glycerol (DAG—e.g. at least one C16 to C18 DAG, such as GDO) with at least one tocopherol. Such mixtures include 2:98 to 98:2 by weight tocopherol:DAG, e.g. 10:90 to 90:10 tocopherol:DAG and especially 20:80 to 80:20 of these compounds. Similar mixtures of tocopherol with other acyl glycerols, such as any of those discussed herein are also suitable.

Component b)—Phospholipid

Optional component "b" in the preferred lipid matrices of the present invention is at least one phospholipid. As with component a), this component comprises a polar head group and at least one non-polar tail group. The difference between components a) and b) lies principally in the polar group. The non-polar portions may thus suitably be derived from the fatty acids or corresponding alcohols considered above for component a). The phospholipid (e.g. PC) will contain two non-polar groups. Again, C18 groups are preferred and may be combined with any other suitable non-polar group, particularly C16 groups. The phospholipids for use in the invention may be those which do not form a non-lamellar liquid crystalline phase structures as a pure compound in water at 25° C. Alternatively, the phospholipids for use in the invention may be those which form a non-lamellar liquid crystalline phase structure, e.g. an hexagonal liquid crystalline phase, in water at 25° C.

The phospholipid portion, even more suitably than any diacyl glycerol portion, may be derived from a natural source. Suitable sources of phospholipids include egg, heart (e.g. bovine), brain, liver (e.g. bovine) and plant sources including soybean. Such sources may provide one or more constituents of component b, which may comprise any mixture of phospholipids.

Suitable polar head groups for component b) include phosphatidylcholine, phosphatidylethanolamine, phosphatidylserine and phosphatidylinositol. Most preferred are phosphatidylcholine (PC) and/or phosphatidylethanolamine (PE). It has been shown in WO2013/038460 and WO2013/083459 that the use of at least 50% PE by weight of the total amount of phospholipid can result in improved depot robustness.

It is known from WO2016/066655 that lipid slow-release matrices based on triacyl lipids can form depot compositions on exposure to aqueous fluids without the need for a phospholipid component to be present, though a phospholipid may also be present. Thus, in one embodiment component a) comprises, consists of or consists essentially of a triacyl lipid(s) and component b) is optional. However, in another embodiment, if component a) includes greater than 50% mono-acyl or diacyl lipids, or at least one tocopherol, or mixtures of any of these components, then a phospholipid component b) will preferably be present. In one embodiment, component a) includes less than 50% (e.g. 0 to 49% or 0.1 to 45%) triacyl lipid (based on the total amount of component a)) and component b) is present (e.g. at 20 to 80 wt % of the pre-formulation or at other amounts as indicated in the various embodiments herein).

In the present invention it is particularly preferred that component b) comprises or consists of one or more PCs. For instance, at least 50% of the head groups of component b) should be PC, preferably more that 65% of the head groups, especially more than 85% or more than 90%. Any single PC or mixture of PCs from these or other sources may be used, but mixtures comprising soy PC or egg PC are highly suitable. The PC component preferably contains at least 50% soy PC or egg PC, more preferably at least 75% soy PC or egg PC and most preferably essentially pure soy PC or egg PC.

In one embodiment applicable to all aspects of the invention, component b) comprises or consists of PC. Preferably the PC is derived from soy. Preferably the PC comprises 18:2 fatty acids as the primary fatty acid component with 16:0 and/or 18:1 as the secondary fatty acid components. These are preferably present in the PC at a ratio of between 1.5:1 and 6:1. PC having approximately 60-65% 18:2, 10 to 20% 16:0, 5-15% 18:1, with the balance predominantly other 16 carbon and 18 carbon fatty acids is preferred and is typical of soy PC.

In an alternative but equally preferred embodiment, also applicable to all aspects of the invention, the PC component may comprise synthetic dioleoyl PC (DOPC). This is believed to provide increased stability and so will be particularly preferable for compositions needing to be stable to long term storage, and/or having a long release period in vivo. In this embodiment the PC component preferably contains at least 50% synthetic dioleoyl PC, more preferably at least 75% synthetic dioleoyl PC and most preferably essentially pure synthetic dioleoyl PC. Any remaining PC is preferably soy or egg PC as above.

In one embodiment, the precursor formulations of the present invention are comprised at least partially of synthetic DOPC (i.e. PC having at least 95% PC head groups and at least 90% oleoyl (C18:1) acyl groups) and has a stability to storage at 15-25° C., defined as less than 5% active agent degradation, as assayed by HPLC, after at least 6 months, more preferably at least 12 months and most preferably at least 24 months.

Since the pre-formulations of the invention are to be administered to a subject for the controlled release of a prostacyclin analogue, it is important that the components are biocompatible. In this regard, the preferred lipid matrices for use in the pre-formulations of the present invention are highly advantageous since both PC and DAGs are well tolerated and are broken down in vivo into components that are naturally present in the mammalian body.

Synthetic or highly purified PCs, such as dioleoyl phosphatidylcholine (DOPC) and palmitoyl oleoyl phosphatidylcholine (POPC), as well as the other various high-purity PCs described herein, are highly appropriate as all or part of component b).

In a highly preferred embodiment, component b) is a "high purity" PC consisting of phospholipids having polar head groups comprising at least 95% phosphatidyl choline, and two acyl chains each independently having 16 to 20 carbons, wherein at least one acyl chain has at least one unsaturation in the carbon chain, and there are no more than four unsaturations over two carbon chains.

Typically, this may be PC with at least 95% PC head groups and at least 95% C16 to C20 acyl chains having 0 to 3 unsaturations.

The synthetic dioleoyl PC is most preferably 1,2-dioleoyl-sn-glycero-3-phosphocholine, and other synthetic PC components include DDPC (1,2-Didecanoyl-sn-glycero-3-phosphocholine); DEPC (1,2-Dierucoyl-sn-glycero-3-phosphocholine); DLOPC (1,2-Dilinoleoyl-sn-glycero-3-phosphocholine); DLPC (1,2-Dilauroyl-sn-glycero-3-phosphocholine); DMPC (1,2-Dimyristoyl-sn-glycero-3-phosphocholine); DOPC (1,2-Dioleoyl-sn-glycero-3-phosphocholine); DPPC (1,2-Dipalmitoyl-sn-glycero-3-phosphocholine); DSPC (1,2-Distearoyl-sn-glycero-3-phosphocholine); MPPC (1-Myristoyl-2-palmitoyl-sn-glycero 3-phosphocholine); MSPC (1-Myristoyl-2-stearoyl-sn-glycero-3-phosphocholine); PMPC (1-Palmitoyl-2-myristoyl-sn-glycero-3-phosphocholine); POPC (1-Palmitoyl-2-oleoyl-sn-glycero-3-phosphocholine); PSPC (1-Palmitoyl-2-stearoyl-sn-glycero-3 phosphocholine); SMPC (1-Stearoyl-2-myristoyl-sn-glycero-3-phosphocholine); SOPC (1-Stearoyl-2-oleoyl-sn-glycero-3-phosphocholine); and SPPC (1-Stearoyl-2-palmitoyl-sn-glycero-3-phosphocholine), or any combination thereof.

A particularly favoured combination of components a) and b) are SMO with PC, GDO with PC, especially GDO with soy PC and/or "high purity" PC. Appropriate amounts of each component suitable for the combination are those amounts indicated herein for the individual components in any combination. This applies also to any combinations of components indicated herein, where context allows.

The ratio of components a:b is in the range 40:60 to 60:40. Preferably the a:b ratio is in the range 45:55 to 55:45, more preferably 47:53 to 53:47. Most preferably the a:b ratio is approximately 50:50, such as 48:52 to 52:48.

In one embodiment, the absolute amount of component a) will be 40 to 47%, the absolute amount of component b) will be 40 to 47%, the ratio of a:b will be 48:52 to 52:48, the amount of component c) will be 5 to 20%, preferably 8 to 12% wherein component c) consists of ethanol and propylene glycol at a ratio of 2.5:1 to 3.5:1, and component d) will be treprostinil sodium at 2.5 to 50 mg/ml (based on free acid), such as 5 to 50 mg/mL (based on free acid).

Component c)—Biocompatible Organic Solvent

Component c) of the pre-formulations of the invention is a biocompatible organic solvent. Since the pre-formulation is to generate a depot composition following administration (e.g. in vivo), typically upon contact with aqueous fluid, it is desirable that this solvent be tolerable to the subject and be capable of mixing with the aqueous fluid, and/or diffusing or dissolving out of the pre-formulation into the aqueous fluid. Solvents having at least moderate water solubility are thus preferred.

Component c) comprises or consists of a biocompatible organic solvent selected from the group consisting of: alcohols including mono-alcoholic solvents and di- and polyalcoholic solvents, amines, amides, sulphoxides or esters. It is particularly preferred that component c) comprises or consists of a mono-alcoholic solvent.

Component c) may comprise two or more components from the list of solvents above, particularly a mono-alcoholic solvent and a solvent selected from amides, sulphoxides or di-alcoholic solvents. Any solvent(s) which is not a mono-alcoholic solvent may be referred to herein as the co-solvent. Where two or more solvents are present especially preferred combinations are ethanol and an amide (such as ethanol and NMP), ethanol and a sulphoxide (such as ethanol and DMSO), or ethanol and a di- or polyalcoholic solvent (such as ethanol and PG). A highly preferred combination of solvents is ethanol and PG, particularly where the ratio of ethanol to PG is 1:5 to 20:1, preferably 1:1 to 10:1, more preferably 1.5:1 to 8:1, most preferably 2:1 to 5:1 (e.g. around 3:1, such as 2.8:1 to 3.2:1). Component c) may comprise or consists of ethanol, propanol, iso-propanol, benzyl alcohol or mixtures thereof. Most preferably component c) comprises or consists of ethanol.

The amount of component c) in the pre-formulation will have a considerable effect upon several features. In particular, the viscosity and the rate (and duration) of release will alter significantly with the solvent level. The amount of solvent will thus be at least sufficient to provide a low viscosity mixture but will additionally be determined so as to provide the desired release rate. This may be determined by routine methods in view of the Examples below. Typically a level of 1 to 30%, particularly 2 to 25% solvent will provide suitable release and viscosity properties. This will preferably be 2 to 20%, preferably 5 to 15% and an amount of around 10% (e.g. 10±3%) is highly effective. These levels include any co-solvent present as part of component c), as mentioned above.

As indicated above, the amount of component c) in the pre-formulations of the invention will be at least sufficient to provide a low viscosity mixture (e.g. a molecular solution) of components a), b), c) and d) and will be easily determined for any particular combination of components by standard methods.

The phase behaviour may be analysed by techniques such as visual observation in combination with polarized light microscopy, X-ray scattering and diffraction techniques, nuclear magnetic resonance, and cryo-transmission electron microscopy (cryo-TEM) to look for solutions, $L_2$ or $L_3$ phases, or liquid crystalline phases or as in the case of cryoTEM, dispersed fragments of such phases. Viscosity may be measured directly by standard means. As described above, an appropriate practical viscosity is that which can effectively be syringed and particularly sterile filtered. This will be assessed easily as indicated herein.

A highly preferred combination for components a), b) and c) is GDO, soy PC and/or "high purity PC", and ethanol, or SMO, soy PC and ethanol. Other preferred combinations include GDO/SPC/ethanol/DMSO, GDO/SPC/ethanol/NMP and GDO/SPC/ethanol/PG. As indicated above, appropriate amounts of each component suitable for the combination are those amounts indicated herein for the individual components, in any combination.

Component c) as used herein may be a single solvent or a mixture of suitable solvents but will generally be of low viscosity. This is important because one of the key aspects of the present invention is that it provides pre-formulations that are of low viscosity and a primary role of a suitable solvent is to reduce this viscosity. This reduction will be a combination of the effect of the lower viscosity of the solvent and the effect of the molecular interactions between solvent and lipid composition. One observation of the present inventors is that the oxygen-containing solvents of low viscosity described herein have highly advantageous and unexpected molecular interactions with the lipid parts of the composition, thereby providing a non-linear reduction in viscosity with the addition of a small volume of solvent.

The viscosity of the "low viscosity" solvent component c) (single solvent or mixture) should typically be no more than 18 mPas at 20° C. This is preferably no more than 15 mPas, more preferably no more than 10 mPas and most preferably no more than 7 mPas at 20° C.

It has been established in WO2012/160213 that the use of an alcohol solvent in combination with a "polar solvent" or "co-solvent" such as a diol or water allows a significant improvement in the performance of certain lipid-based controlled-release compositions. In particular, the addition of a diol (such as propylene glycol) or water has been observed to allow the proportion of alcohol to be increased without adversely affecting the release profile and/or allow an improvement in the release profile and/or allow higher loading of the active agent.

Typical co-solvents will have a comparatively high dielectric constant corresponding to their high polarity. Thus, suitable co-solvents will generally have a dielectric constant of at least 28 at 25° C., more preferably at least 30 at 25° C. Highly suitable examples include water (~80), propylene glycol (~32), dimethylsulphoxide (~47) and N-methyl-2-pyrrolidone (NMP, ~32).

In some embodiments a particularly appropriate combination of solvents for component c) include a mono-alcoholic solvent and a co-solvent selected from the group consisting of: amides, sulphoxides or diols. An especially preferred combination is ethanol and an amide, ethanol and a sulphoxide or ethanol and a diol. Particularly preferred combinations are ethanol and propylene glycol (PG); ethanol and dimethylsulphoxide (DMSO); and ethanol and N-methyl-pyrrolidone (NMP).

When present, a suitable amount of the co-solvent will typically be greater than 1% by weight of the pre-formulation, for example 2-15%, particularly 4-12.%, especially 4-10 wt. %. The combination of a mono-alcoholic solvent and a co-solvent as component c) has potential advantages in the compositions of the invention. In particular, by inclusion of some co-solvent which is miscible with the mono-alcohol component, the slight sensation that may be caused at the injection site from the alcohol content can be substantially eliminated. Thus, in one embodiment, the ratio of mono-alcoholic component:co-solvent may be in the range 30:70 to 90:10, more preferably 50:50 to 80:20, especially 60:40 to 80:20. Approximately equal amounts of components (w/w) are highly appropriate.

Component d)—Prostacyclin Analogue

The pre-formulations of the present invention contain at least one prostacyclin analogue or a salt thereof. Prostacyclin and synthetic analogues beraprost, epoprostenol, iloprost and treprostinil are shown below.

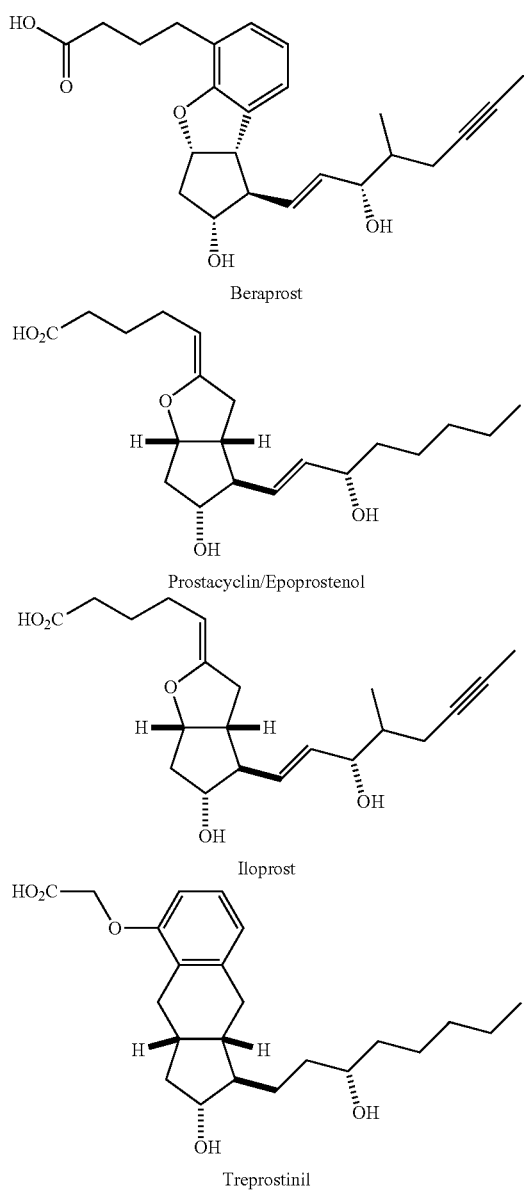

Beraprost

Prostacyclin/Epoprostenol

Iloprost

Treprostinil

The choice of the prostacyclin analogue is not particularly critical to the invention so long as it achieves the therapeutic effects desired and does not adversely affect the phase behaviour of the pre-formulation.

Typically however, the prostacyclin analogue component d) will have one or more of the following features. Firstly, it is preferably a synthetic non-peptide. Secondly, it preferably has a molecular weight of below 500 amu, preferably below 400 amu (free acid). Thirdly, it preferably comprises a cyclopentane unit having a 1-hydroxy substituent, a C3-12 alkyl, alkenyl or alkynyl group at the 2-position, and a 3,4-cis fused 5- or 6-membered ring. The numbering used will be readily understood with reference to the structures given above. Fourthly, the prostacyclin analogue preferably comprises a carboxylic acid and/or an ester unit. As can be seen from the structures of beraprost, epoprostenol, iloprost and treprostinil, these structural features are shared between prostacyclin and the known synthetic analogues beraprost, iloprost and treprostinil.

The prostacyclin analogue for use in all aspects of the invention may particularly include a prostacyclin analogue of formula (I):

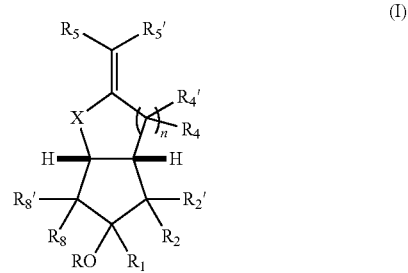

wherein:

n is 1 or 2;

X is O, $CH_2$, CHF or $CF_2$;

R is H, R10, or is attached by a linking unit to a polyethylene glycol (PEG);

R1 is H, F or C1-C10 substituted or unsubstituted alkyl, alkenyl or alkynyl;

R2' is H, F or C1-C6 substituted or unsubstituted alkyl, alkenyl or alkynyl;

R2 is a saturated or unsaturated C1-12 substituted or unsubstituted alkyl, alkenyl or alkynyl group, preferably a saturated or unsaturated C1-10 group;

R5 is $X(CH_2)_aCO_2R9$, wherein X is O or $CH_2$, a is 0 to 4, preferably 1 or 2, and wherein R9 is H, C1-C6 substituted or unsubstituted alkyl, alkenyl or alkynyl or a biologically acceptable cation;

R8 and R8' are each independently H, F or C1-C6 alkyl, alkenyl or alkynyl, preferably H;

n is 1 or 2;

and either:

All R4 and R4' groups are each independently H, F or C1-C6 substituted or unsubstituted alkyl, alkenyl or alkynyl; and R5' is H, F or a C1-C6 substituted or unsubstituted alkyl, alkenyl or alkynyl group, preferably H;

or:

R5' and the neighbouring R4 and/or R4' groups form a 5, 6 or 7 membered substituted or unsubstituted ring, preferably a 6-membered ring and most preferably a substituted or unsubstituted 6-membered aromatic ring; and any additional R4 and/or R4' groups are each independently H, F or C1-C6 substituted or unsubstituted alkyl, alkenyl or alkynyl.

R10 is a group such a protective or prodrug moiety. Suitable protective and/or prodrug moieties include esters including those defined in subsequent sections.

In a preferred embodiment, if n is 1 then the structure is either of Formula (I-a)

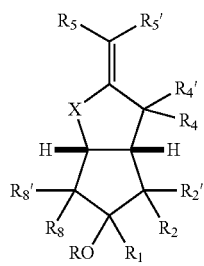
(I-a)

in which R4 and R4' are each independently H, F or C1-C6 alkyl, preferably H; and
R5' is H, F or a C1-C6 alkyl group, preferably H;
with the remaining substituents as defined above for Formula (I);
or of structure Formula (I-b)

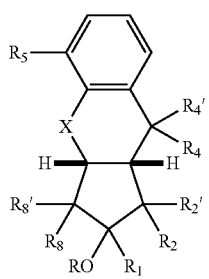
(I-b)

with the substituents are as defined above for Formula (I);
In a further preferred embodiment, if n is 2 then the structure is of Formula (I-c)

(I-c)

in which R4 and R4' are each independently H, F or C1-C6 alkyl, preferably H;
with the remaining substituents as defined above for Formula (I).
The following are particularly preferred embodiments.
For each of Formula (I), (Ia), (Ib) and (Ic):
X is preferably O or $CH_2$;
R1 is preferably H;
R2 preferably includes an OH group attached to the third carbon atom of R2 from the cyclopentane unit;
R2' is preferably H;
R4 and R4' are all preferably H or form a phenol ring with R5';
R8 and R8' are both preferably H;

In addition to the above preferred embodiments, for Formula (Ia):
R2 is preferably an unsaturated C6-C12 group, preferably an unsaturated C8-C10 group, especially including an OH group attached to the third carbon atom of R2 from the cyclopentane unit. Still more preferably R2 is

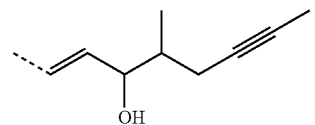

even more preferably R2 is:

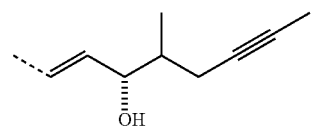

or R2 is:

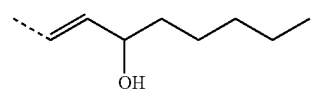

or R2 is:

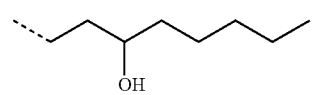

even more preferably R2 is:

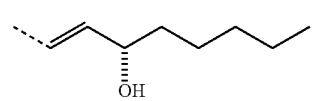

or R2 is:

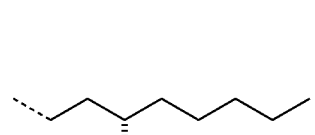

R5' is preferably H;
X is O or $CH_2$;
R5 is preferably $CH_2CH_2CH_2CO_2R^9$, where $R^9$ is as defined above, especially $CH_2CH_2CH_2CO_2H$;
R is preferably H.
In an embodiment the prostacyclin analogue may be iloprost.
For Formula (Ib):
R2 is preferably an unsaturated C6-C12 group, preferably an unsaturated C8-C10 group, especially including an OH group attached to the third carbon atom of R2 from the cyclopentane unit. Still more preferably R2 is even more preferably R2 is:

X is preferably O;
R5 is preferably $CH_2CH_2CH_2CO_2R^9$, where $R^9$ is as defined above, especially $CH_2CH_2CH_2CO_2H$;
R is preferably H.
In an embodiment the prostacyclin analogue may be beraprost.
For Formula (Ic):
X is preferably $CH_2$;
R is preferably H or attached via a linking group to a PEG;
R2 is preferably a saturated C6-C10 group, preferably a saturated C8 group, especially including an OH group attached to the third carbon atom of R2 from the cyclopentane unit. Still more preferably R2 is:

or R2 is:

even more preferably R2 is:

or R2 is:

R5 is preferably $OCH_2CO_2R^9$, where $R^9$ is as defined above, most preferably $OCH_2CO_2H$.
In an embodiment the prostacyclin analogue may be treprostinil.
In any of the formulae indicated herein, where an OH group is present (especially as group OR or as an element of group $R_2$), such a group may be protected as a pro-drug. Such prodrugs are typically hydrolysed in vivo to re-generate the free OH moiety and may include ester and/or acetal groups. Particularly suitable prodrugs are as described for the R1 and R2 positions in U.S. Pat. No. 9,394,227, incorporated herein in its entirety.
In such cases where an OH moiety is protected as a pro-drug, any OH group may independently be protected as a —O—R10 group, where R10 in each occurrence independently is one of the following:

$R_{11}$ in each occurrence independently is alkyl, alkylaryl, cycloalkyl, heterocyclyl, aryl or heteroaryl, each of which may optionally be substituted;
$R_{12}$ and $R_{13}$ in each occurrence independently are hydrogen, C1-C6 alkyl or C3-C6 cycloalkyl, or $R_{12}$ and $R_{13}$ and the carbon atom to which they are connected form a C3-C6 cycloalkyl ring;
$R_{14}$ in each occurrence independently is hydrogen, $R_{11}$, —C(=O)$R_{11}$, —C(=O)O$R_{11}$ or or —C(=O)N$R_{15}R_{16}$; or
$R_{14}$ and $R_{12}$ or $R_{13}$, together with the atoms to which they are connected, form a heterocyclic ring;
$R_{15}$ and $R_{16}$ in each occurrence independently are hydrogen, alkyl, -alkylaryl, cycloalkyl, heterocyclyl, aryl or heteroaryl; or
$R_{15}$ and $R_{16}$ and the nitrogen atom to which they are connected form a heterocyclic or heteroaryl ring;
j in each occurrence independently is an integer from 0 to 4; and
m in each occurrence independently is an integer from 1 to 10.
In certain embodiments, R11 in each occurrence independently is methyl, ethyl, propyl, isopropyl, butyl, iso-butyl, sec-butyl or tert-butyl; R12 and R13 in each occurrence independently are hydrogen, methyl, ethyl, propyl or isopropyl; R14 in each occurrence independently is hydrogen or R11; j is 0; and m is 1.
Where a substitution is made for an OH group, this may be independently at any one OH group or preferably will be at all free OH groups. In one preferred embodiment, all —OH groups present as OR or as a part of group R2 will be protected with the same prodrug —O—R10 group. In some embodiments any one or each of the —OH groups present are substituted for an ester.
Some particular example esters that may be used to substitute "—OH" groups to provide prodrugs include ethyl, isopropyl or succinate esters.
In all embodiments in which the prostacyclin analogue d) is a pro-drug it is preferred that the pro-drug is formulated in a pre-formulation comprising:

a) at least one of a mono-, di- or tri-acyl lipid and/or a tocopherol;
b) optionally at least one phospholipid; and
c) at least one biocompatible, organic solvent; and
and wherein the pre-formulation forms, or is capable of forming, at least one liquid crystalline phase structure upon contact with excess aqueous fluid.

In particular, in all embodiments in which the prostacyclin analogue d) is a pro-drug it is preferred that the pro-drug is formulated in a pre-formulation comprising:
a) a diacyl lipid, most preferably glycerol dioleate (GDO);
b) at least one phospholipid, preferably phosphatidyl choline (PC); and
c) at least one biocompatible, organic solvent; and
and wherein the pre-formulation forms, or is capable of forming, at least one liquid crystalline phase structure upon contact with excess aqueous fluid.

In all embodiments the geometry of the ring system according to Formula (I) is preferably:

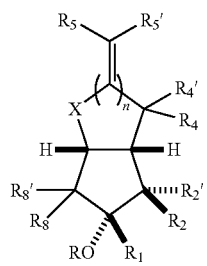

In a preferred embodiment the prostacyclin analogue has a molecular weight of less than 500 g/mol.

Most preferably component d) comprises or consists of beraprost, epoprostenol, iloprost or treprostinil (e.g. epoprostenol, iloprost or treprostinil), most preferably treprostinil. Any biologically acceptable salt of the prostacyclin analogue may also be used. Where amounts of component d) are given as a percentage by weight, the weight based on the free acid is meant unless context allows otherwise. In a particularly preferred embodiment component d) comprises or consists of treprostinil free acid (TPN) or a salt thereof, most preferably treprostinil sodium salt (TPN(Na)). The use of ester derivatives, such as ethyl esters or esters of other biologically tolerable alcohols (including diols or polyhydroxy alcohols such as propylene glycol or glycerol) is also envisaged and may provide a "prodrug" effect which may be useful in controlling the release of the prostacyclin analogue and/or its biological half-life.

Indicated herein is the optional use of a "linking unit" or "linker", particularly at the "R" position of formula (i) or the corresponding site on other structures. Such a linker may, for example, form an ester linkage at position R and may join a larger moiety such as a peptide, protein, PEG group by means of straight-chain, branched and/or cyclic alkyl and/or alkenyl moieties, ester groups, amide groups, amine groups, ether groups, thiols, thioesters and cyclic moieties such as pyrrolidine and pyrrolidinedione (e.g. 3-Sulfanyl-2,5-pyrrolidinedione) groups, any of which may be substituted or unsubstituted as required.

Other prostacyclin analogues suitable for use in the invention include all prostacyclin-receptor agonists such as Selexipag.

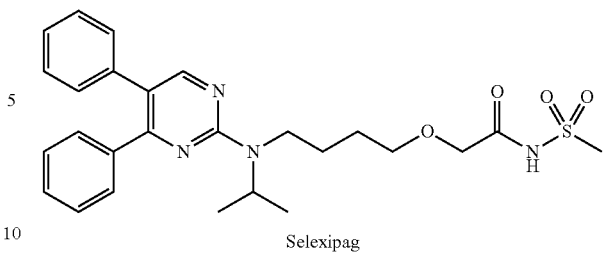

Selexipag

Component d) is present in an amount of 0.1 to 15% based on the prostacyclin analogue free acid, preferably 0.1 to 10%, such as 1 to 12%, especially 2 to 8%. In some embodiments the level of prostacyclin analogue may be 4 to 8%. These levels are particularly suitable for treprostinil.

It is a surprising finding of the inventors that the release duration of prostacyclin analogue such as treprostinil is strongly dependent on both the amount of active agent and the nature of the solvent component c). Accordingly, the release properties of the depot may be tuned by varying one or more of these parameters.

It is furthermore a surprising finding of the present inventors that the release of prostacyclin analogue such as treprostinil can be effectively controlled by appropriate selection of formulation solvent and solvent ratio.

In general with depot formulations of mono- and/or diacyl lipids (such as GDO) with phospholipids such as phosphatidyl choline, the release of active agent is primarily controlled by the phase behaviour of the formulation, which in turn is primarily controlled by the nature and proportion of the lipid components. In the present case, however, the inventors have established that the release properties, and in particular the maximum in vivo concentration reached following administration (Cmax) can be usefully optimised by choice of solvent and solvent ratio. In one embodiment, for example, the present invention provides precursor formulations of the present invention where component c) comprises, comprises essentially of or consists of ethanol and propylene glycol wherein the ratio of ethanol to PG is between 1:1 and 10:1, more preferably 1.5:1 to 8:1, most preferably 2:1 to 5:1 (e.g. around 3:1). In particular, formulations having both ethanol and PG (e.g. at least 0.5% of each) where the amount of ethanol is greater than the amount of PG may provide a lower Cmax (i.e. a lower "peak" in vivo concentration) than formulations where there is an equal or lesser amount of ethanol in comparison with PG. Such control of release properties is of great importance in a slow-release formulation and would not be expected to be provided by choice of solvent ratio.

Figure 4A:
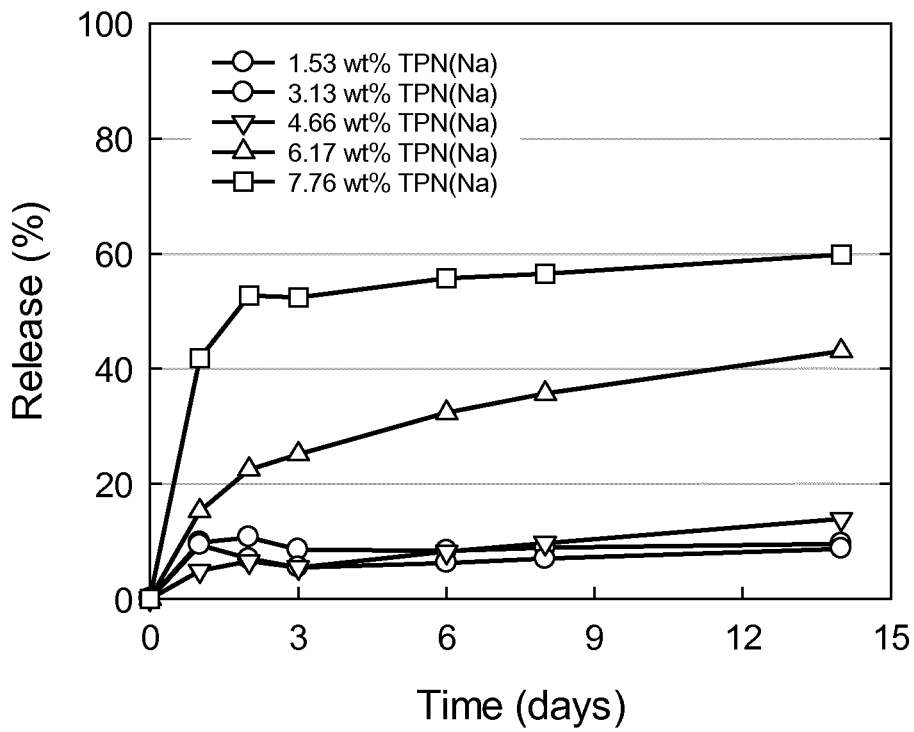

With regard to the level of component d), FIG. 4a illustrates the in vitro release of TPN from formulations containing between 1.53 to 7.76% TPN(Na) in a matrix of GDO/PC/EtOH (45:45:10). At loadings of 7.76% TPN(Na) the formulations exhibit "burst" characteristics, i.e. about 50% of the TPN(Na) is released after a period of about 24 hours, whereas at levels of 6.17% and below, the release of TPN(Na) is much more gradual. Being able to alter the burst profile simply by appropriate choice of components is potentially a very useful feature of pre-formulations of the invention. In one embodiment, these may be affected by choice of solvent and solvent ratio.

In one embodiment, particularly where it is desired that the formulation provides a short-term release over 1 to 3 days, it may be desirable to operate with a level of prostacyclin analogue, especially TPN or TPN(Na), of 6.5% or more, especially 6.7% or more, or 7% or more. However, in general the level of prostacyclin analogue will typically be no more than 5% by weight, preferably no more than 4% by weight (e.g. 0.5 to 4% by weight, such as around 1%, around 2% or around 3% by weight).

Short term release depots providing an effective release over a period of 1 to 3 days may be formulated with ethanol as the only component c) a level of at least 11%, preferably at least 12%, especially at least 13%. Alternatively, a mixture of ethanol and a sulfoxide, especially ethanol and DMSO may be used as component c) in an amount of 20% or less, such as 10 to 20%, especially 12 to 18%. In this embodiment the ratio of ethanol:sulfoxide is in the range of 20:80 to 60:40 (w:w), especially in the range of 30:70 to 50:50.

Where it is desired to provide a more gradual release of prostacyclin analogue, for instance for a week-long or fortnightly or monthly duration depot, it may be desirable to operate with levels of d), of less than 6.5%, such as 6.2% or less, especially 5.5% or less or 5% or less may be desirable. As noted above, the level of prostacyclin analogue will typically be no more than 5% by weight, preferably no more than 4% by weight (e.g. 0.5 to 4% by weight, such as around 1%, around 2% or around 3% by weight). Thus, a pre-formulation for once weekly or once fortnightly administration may preferably comprise 1 to 7% of prostacyclin analogue, such as 1 to 3%, especially of TPN or TPN(Na).

Long term release depots providing an effective release over a period of greater than 5 days, such as weekly or fortnightly may be formulated with ethanol as the only component c) at a level of less than 11%, such as 10% or less. Alternatively, a mixture of ethanol and a di- or polyalcoholic solvent, especially ethanol and PG or ethanol and water may be used in an amount of 5 to 20%, especially 5 to 15%, with a ratio of ethanol:PG or ethanol:water in the range of 40:60 to 60:40 (w:w), levels of about 50:50 are particularly preferred. An amount of around 2.5% PG and around 7.5% ethanol is highly effective.

In one aspect each of the embodiments herein can optionally contain an antimicrobial or microbial-static agent, which includes bacteriostatic agents and preservatives. Such agents include benzalkonium chloride, m-cresol, benzyl alcohol or other phenolic preservatives. Typical concentrations as known in the art can be used.

Additional components above those mentioned as components a) to d) will, where present at all, preferably be present in an amount of 0 to 5% (e.g. 0.01% to 5%) by weight, preferably no more than 2% by weight and more preferably no more than 1% by weight.

In one embodiment, components a) and b) (allowing for any impurity inherent in the nature of these components) make up at least 95% of the lipid components of the composition. Preferably at least 99% of the total lipid content of the pre-formulation consists of components a) and b). Preferably the lipid component of the pre-formulation consists essentially of components a) and b).

Administration

The pre-formulations of the present invention are generally formulated to be administered parenterally. This administration will generally not be an intra-vascular method but will preferably be subcutaneous (s.c.), intracavitary or intramuscular (i.m.). Importantly, pre-formulations of the invention have the advantage that they do not need to be administered either intravenously or by continuous s.c. injection. Preferably the administration is not intravenous or continuous s.c.

Typically the administration will be by injection, which term is used herein to indicate any method in which the formulation is passed through the skin, such as by needle, catheter or needle-less (needle-free) injector. Preferred parenteral administration is by i.m or s.c. injection, most preferably by s.c. injection. An important feature of the composition of the invention is that it can be administered both by i.m. and s.c. and other routes without toxicity or significant local effects, especially without causing significant site pain. It is also suitable for intracavital administration. The s.c. injection has the advantage of being less deep and less painful to the subject than the (deep) i.m. injection and is technically most suitable in the present case as it combines ease of injection with low risk of local side effects. It is a surprising observation of the present inventors that the formulations provide sustained release of active agent over a predictable time period by subcutaneous injection, and typically much longer release durations are made available by formulations of the invention compared with existing formulations of prostacyclin analogues.

The preferred lipid pre-formulations of the present invention provide non-lamellar liquid crystalline depot compositions upon exposure to aqueous fluids, especially in vivo. As used herein, the term "non-lamellar" is used to indicate a normal or more preferably reversed liquid crystalline phase (such as a reversed cubic or hexagonal phase) or the L3 phase or any combination thereof. The term liquid crystalline indicates all hexagonal, all cubic liquid crystalline phases and/or all mixtures thereof. Hexagonal as used herein indicates "normal" or "reversed" hexagonal (preferably reversed) and "cubic" indicates any cubic liquid crystalline phase unless specified otherwise. The skilled reader will have no difficulty in identifying those compositions having appropriate phase behaviour by reference to the description and Examples provided herein, and to WO2005/117830, but the most favoured compositional area for phase behaviour is where ratio of components a:b are as described in the preceding sections. Ratios of around 50:50 (e.g. ±2) are highly preferred for most formulations, most preferably around 50:50.

It is important to appreciate that the pre-formulations of the present invention are of low viscosity. As a result, these pre-formulations must not be in any bulk liquid crystalline phase since all liquid crystalline phases have a viscosity significantly higher than could be administered by syringe or similar injecting dispenser. The pre-formulations of the present invention will thus be in a non-liquid crystalline state, such as a solution, $L_2$ or $L_3$ phase, particularly solution or $L_2$. The $L_2$ phase as used herein throughout is preferably a "swollen" $L_2$ phase containing greater than 5 wt %, preferably greater than 7%, and most preferably greater than 9% of organic solvent (component c) having a viscosity reducing effect. The pre-formulations of the invention which are in $L_2$ phase form one preferred set of pre-formulations.

As used herein, the term "low viscosity mixture" or "low viscosity pre-formulation" is used to indicate a mixture which may be readily administered to a subject and in particular readily administered by means of a standard syringe and needle arrangement. This may be indicated, for example by the ability to be dispensed from a 1 ml disposable syringe through a small gauge needle. Preferably, the low viscosity mixtures can be dispensed through a needle of 19 gauge, preferably smaller than 19 gauge, more preferably 23 gauge (or most preferably even 27 gauge) needle by manual pressure. In a particularly preferred embodiment, the low viscosity mixture should be a mixture capable of passing through a standard sterile filtration membrane such as a 0.22 μm syringe filter. A typical range of suitable viscosities would be, for example, 10 to 1000 mPas, more preferably 10 to 800 mPas and most preferably 200 to 700 mPas at 20° C.

Upon administration, the preferred lipid-based pre-formulations of the present invention undergo a phase structure transition from a low viscosity mixture to a high viscosity (generally tissue adherent) depot composition. Generally this will be a transition from a molecular mixture, swollen $L_2$ and/or $L_3$ phase to one or more (high viscosity) liquid crystalline phases such as reversed hexagonal or cubic liquid crystalline phases or mixtures thereof. Further phase transitions may also take place following administration. Obviously, complete phase transition is not necessary for the functioning of the invention but at least a surface layer of the administered mixture will form a liquid crystalline structure. Generally this transition will be rapid for at least the surface region of the administered formulation (that part in direct contact with air, body surfaces and/or body fluids). This will most preferably be over a few seconds or minutes (e.g. from 1 second up to 30 minutes, preferably up to 10 minutes, more preferably 5 minutes of less). The remainder of the composition may change phase to a liquid crystalline phase more slowly by diffusion and/or as the surface region disperses.

Without being bound by theory, it is believed that upon exposure to excess aqueous fluid, the pre-formulations of the invention lose some or all of the organic solvent included therein (e.g. by diffusion) and take in aqueous fluid from the bodily environment (e.g. the in vivo environment). For lipid pre-formulations, at least a part of the formulation preferably generates a non-lamellar, particularly liquid crystalline phase structure. In most cases these non-lamellar structures are highly viscous and are not easily dissolved or dispersed into the in vivo environment. The result is a monolithic "depot" generated in vivo with only a limited area of exposure to body fluids. Furthermore, because the non-lamellar structure has large polar, apolar and boundary regions, the lipid depot is highly effective in solubilising and stabilising active agents and protecting these from degradation mechanisms. As the depot composition formed from the pre-formulation gradually degrades over a period of days, weeks or months, the active agent is gradually released and/or diffuses out from the composition. Since the environment within the depot composition is relatively protected, the pre-formulations of the invention are highly suitable for active agents with a relatively short biological half-life.

By incorporation of at least 2% (e.g. at least 5%) of a polar co-solvent (especially at least 5% PG, water, NMP or DMSO) into the pre-formulations, it is believed that the rate of phase transition to a non-lamellar (e.g. liquid crystalline) phase at the surface of the injected pre-formulation can be enhanced in comparison with compositions containing organic solvents in the substantial absence of water. The performance of the resulting depot is thus improved and further control over the release of active agent achieved.

The depot systems formed by the formulations of the present invention are highly effective in protecting the active agent from degradation and thus allow an extended release period. The formulations of the invention thus may provide in vivo depots of prostacyclin analogue which require administration only once every 1 to 60 days. Typical administration intervals will be, for example, every 1, 2, 3, 7, 14, 21, 28, 30, or 60 days and may be varied either systematically or occasionally by small amounts (e.g. by ±3 days, or by ±20% in any appropriate case). Highly preferred administration frequencies include every 7 (±1) days or every 14 (±2) days, or every 30 (±3) days. In one embodiment, formulations containing a comparatively low level of prostacyclin analogue (e.g. 0.5 to 2.0%) may be administered once weekly, once fortnightly, or once monthly, and formulations having a higher level of prostacyclin analogue (e.g. 2.5% to 4% or greater by weight) may be administered once weekly or more frequently, such as once every 3 days, once every 2 days or daily.

Evidently, a longer stable release period is desirable for patient comfort and compliance, as well as demanding less time from health professionals if the composition is not to be self-administered. Where the composition is to be self-administered, patient compliance may be aided by a weekly (e.g. every 7 days, optionally ±1 day) or monthly (e.g. every 28 or 30 days (optionally ±7 days)) administration so that the need to administer is not forgotten. Even providing a formulation which did not need to be administered continuously or more than once daily would greatly improve patient wellbeing in this field in many cases.

In one embodiment of the present invention, applicable to all aspects but particularly the methods of treatment and corresponding uses, administration dose and frequency may be gradually escalated to correspond with the progression of the underlying disease (such as any of those diseases indicated herein). Thus, dosages of 1 mg/week or 5 mg/week of prostacyclin analogue may be sufficient for a subject at an early stage and these may be provided as weekly, fortnightly or monthly administrations as needed (e.g. a 1.5 ml injection at 10 mg/ml every 4 weeks would give an average dose of 3.75 mg/week and may be sufficient for an early stage of the disease. As the disease progresses, dosages may be increased to 1 ml (at 10 mg/ml) every fortnight, (5 mg/week), 0.75 ml every week (7.5 mg/week) and 1.0 ml/week (10 mg/week). Subsequent increases may then be achieved by higher concentrations of formulation, such as 1.0 ml of 30 mg/ml formulation every fortnight (15 mg/week), rising by increasing frequency and volume to, for example to 1.0 ml weekly (30 mg/week) and then if necessary to multiple administrations per week.

Initial doses of known prostacyclin analogues using continuous infusion of around 1 to 4 ng/kg/min are typical as starting infusion doses, corresponding to around 10 to 40 μg/kg per week, particularly for epoprostenol and its salts (e.g. sodium salt). Such doses form suitable starting doses for the formulations of the present invention, which may then be titrated up until a suitable efficacy/tolerability balance is achieved. For treprostinil (and salts such as sodium salt), suitable starting doses are typically around half that of epoprostenol, corresponding to 0.5 to 2 ng/kg/min (around 5 to 20 μg/kg per week). Again, up-titration can be applied until a suitable dose is established.

It is an important aspect of the administration methods of the present invention that although the precursor formulations described herein will preferably provide controlled release of the prostacyclin analogue for at least 7 days, the administration frequency may be more rapid than this. Thus, for example, the plasma concentration of prostacyclin analogue at 7-days following a single injection of the pre-formulations of the present invention may drop to no lower than $10^{-3}$, preferably no lower than $10^{-2}$ and most preferably no less than $10^{-1}$ of the plasma concentration at the end of day 1 following that administration. Such a controlled-release performance may be sufficient for a 7-day duration product at an early stage of the disease and provides a significant advantage in that respect. However, the administration of such a product having release properties as described may be repeated more frequently than every 7 days (e.g. twice a week, every 3 days, every 2 days or daily). This administration will take place significantly before the effects of the first administration cease to be effective. However, multiple injections (e.g. at multiple sites) of long-duration products described herein provide for an still greater levelling of the prostacyclin analogue plasma concentration and allow very high doses without needing large injection volumes.

Thus, for example, twice-weekly injection of 1.0 ml of 30 mg/ml formulation will provide 60 mg/week without any large injections and with a very stable release profile since the "peak" of one release corresponds to the stable plateau level of the previous administration. In this way, pre-formulations of the present invention having a notional 7-day or greater duration (e.g. a 7-day release profile described above) may be used twice a week, every 3 days, every 2 days or daily to provide high and stable concentrations of prostacyclin analogue when progression of disease mandates that.

Another considerable advantage of the depot precursors of the present invention is that they are stable homogeneous phases. That is to say, they may be stored for considerable periods (preferably at least 6 months, especially at least 12 months) at room or refrigerator temperature, without phase separation. As well as providing advantageous storage and facile administration, this allows for the dose of prostacyclin analogue to be selected by reference to the species, age, sex, weight, and/or physical condition of the individual subject, by means of injecting a selected volume.

The present invention thus provides for methods comprising the selection of a dosing amount specific to an individual, particularly by subject weight. The means for this dose selection is the choice of administration volume.

The pre-formulations of the present invention are highly advantageous in that they are stable to prolonged storage in their final "administration ready" form. As a result, they may readily be supplied for administration either by health professionals or by patients or their careers, who need not be fully trained health professionals and may not have the experience or skills to make up complex preparations. This is particularly important in long-duration, slow-effecting diseases such as diabetes.

PDE5 Inhibitors

In a further aspect of the present invention, the precursor formulations of the present invention will comprise at least one prostacyclin or prostacyclin analogue, such as those described herein, and may additionally comprise at least one PDE5 inhibitor.

PDE5 inhibitors have typically been administered for immediate treatment of erectile dysfunction (ED) and have advantageously been provided in fast-acting formulations. PDE5 inhibitors at suitable doses, however, have been indicated and/or tested in the long-term treatment of several clinically significant conditions including Pulmonary Arterial Hypertension (PAH). As such, suitable does of PDE5 inhibitors may be added to any of the formulations of the present invention in order to provide a dual effect treatment.

Suitable PDE5 inhibitors include known inhibitors such as avanafil, lodenafil, mirodenafil, sildenafil, tadalafil, vardenafil, udenafil, zaprinast, Icariin (and synthetic derivatives thereof), benzamidenafil, dasantafil, salts, prodrugs and mixtures thereof. Highly suitable PDE5 inhibitors include Tadalafil (Cialis) and vardenafil (Levitra).

Doses of PDE5 inhibitor suitable for a once-weekly administration would typically be in the range 1 to 75 mg PDE5 inhibitor (calculated as free base or unprotected drug molecule), preferably 2 to 50 mg per week (i.e. per administration) and most preferably 5 to 25 mg per week.

Doses of PDE5 inhibitor suitable for a once-fortnightly administration would typically be in the range 2 to 150 mg PDE5 inhibitor (calculated as free base or unprotected drug molecule), preferably 5 to 100 mg per fortnight (i.e. per administration) and most preferably 10 to 50 mg per fortnight.

Doses of PDE5 inhibitor suitable for once-monthly administration would typically be in the range 5 to 300 mg PDE5 inhibitor (calculated as free base or unprotected drug molecule), preferably 10 to 200 mg per month (i.e. per administration) and most preferably 20 to 100 mg per month.

Alternatively, the depot precursors of the present invention may be administered concomitantly with an equivalent formulation comprising at least one PDE5 inhibitor (i.e. one administration of a pre-formulation containing a prostacyclin analogue and another administration of a pre-formulation containing a PDE5 inhibitor). Such concomitant administration may be simultaneous or sequential in either order but will typically be on the same day and with depot precursor formulations having similar durations (e.g. both will be monthly formulations or both weekly). Preferably concomitant administration will be of precursor formulations which comprise similar controlled-release matrices (e.g. both lipid or both polymer, such as any of the preferred systems indicated herein) and most preferably will be of precursor formulations which are both lipid formulations and which comprise the same or substantially the same lipid components (optionally with the same or substantially the same solvent components). Most preferred components will include DAGs (e.g. GDO) and phospholipids (e.g. PC) as described herein.

Devices

In a yet further aspect, the present invention provides a disposable administration device (which is also to include a device component) pre-loaded with a measured dose of a pre-formulation of the present invention. Such a device will typically contain a single dose ready for administration, and will generally be sterile-packed such that the composition is stored within the device until administration. Suitable devices include cartridges, ampoules and particularly syringes and syringe barrels, either with integral needles or with standard (e.g. luer) fittings adapted to take a suitable disposable needle. Similarly appropriate devices include a needle-less injector, a multi- or single-use autoinjector combined with a pre-filled syringe, a cartridge, optionally combined with a multi-use pen device, or a vial. Evidently, such pre-filled syringes and cartridges may be for any appropriate injecting device, such as a multi-use or single-use injector or needle-less injection unit.

The devices of the invention may preferably contain the pre-formulation of the invention which delivers a dosage in the range of 2 to 50 mg/ml, preferably 5 to 40 mg/ml, most preferably 7 to 35 or 10 to 30 mg/ml. Dose volumes will typically be no more than 2 ml (e.g. 0.1 to 2 ml), for example 0.25 to 1.5 ml or 0.5 to 1 ml. A formulation which is administered weekly or more often may preferably be no more than 1.2 ml or 1.0 ml in volume where a formulation for fortnightly or monthly administration may preferably be no more than 2 ml or 1.5 ml in volume.

In one embodiment applicable to all aspects of the invention, the devices of the invention may contain a single dose of 1 to 200 mg, for example 2 to 150 mg (e.g. 5 to 120 mg) of prostacyclin analogue.

The devices of the invention may contain prostacyclin analogue at around 0.005 to 2.5 mg/kg/week, preferably at a level of 0.01 to 1 mg/kg/week, especially 0.015 to 0.7 mg/kg/week. Doses for a 50 kg, 70 kg or 80 kg subject, as well as all other subjects or ranges of subject weights may be calculated correspondingly. For instance, a suitable dose of prostacyclin analogue for a 70 kg subject would be in the range of 0.35 to 175 mg/week, preferably 0.7 to 70 mg/week, especially 1 to 50 mg/week.

The devices of the invention may contain a total volume for administration of no more than 2 ml, preferably no more than 1 ml, especially no more than 0.5 ml.

The pre-filled devices of the invention may also suitably be included in an administration kit, which kit also forms a further aspect of the invention. In a still further aspect, the invention thus provides a kit for the administration of at least one prostacyclin analogue, said kit containing a measured dose of a formulation of the invention and optionally an administration device or component thereof. Preferably the dose will be held within the device or component, which will be suitable for i.m. or preferably s.c. administration. The kits may include additional administration components such as needles, swabs, etc. and will optionally and preferably contain instructions for administration. Such instructions will typically relate to administration by a route as described herein and/or for the treatment of a disease indicated herein above.

Kits

The invention provides for a pre-filled administration device as indicated herein and a kit as indicated herein comprising a pre-formulation as described herein. Suitable kits may include a single- or multiple-use injection device such as an auto-injector or may include cartridges or components for use in such devices.

Kits of the present invention will additionally (optionally but preferably) include any of the following components:
  i) an injection device such as a syringe or auto-injector
  ii) a dose-measurement device (e.g. a graduated device for measuring or setting administration volume)
  iii) a table, chart, phone app' or electronic calculator for calculating and/or setting dosage volume based on parameters such as subject weight and/or dose frequency. Factors such as disease progression and/or prostacyclin analogue concentration may be accounted for in such calculations, either explicitly or implicitly.
  iv) instructions for dosing and/or for escalation of dosing according to factors such as subject weight and/or dose frequency, disease progression (e.g. mean pulmonary artery pressure) and/or prostacyclin analogue concentration.

Preferred Features and Combinations

In combination with the features and preferred features indicated herein, the pre-formulations of the invention may have one or more of the following preferred features independently or in combination:

All proportions indicated herein may optionally be varied by up to 10% of the amount specified, optionally and preferably by up to 5%;

Component a) comprises, consists essentially of or preferably consists of GDO;

Component b) comprises, consists essentially of or preferably consists of soy PC and/or "high purity PC" such as DOPC;

Component c) comprises, consists essentially of or consists of a 1, 2, 3 or 4 carbon alcohol, preferably isopropanol or more preferably ethanol;

Component c) comprises, a polar solvent such as water, NMP, DMSO, propylene glycol, or mixtures thereof;

The pre-formulation has a low viscosity as indicated herein.

The pre-formulation comprises forms a liquid crystalline phase as indicated herein upon in vivo administration.

The pre-formulation generates a depot following in vivo administration, which depot releases at least one prostacyclin analogue over a period of at least 3 days, preferably at least 5 days, more preferably at least 7 days.

The pre-formulation generates a depot following in vivo administration to a subject, which depot releases at least one prostacyclin analogue such that the plasma concentration of prostacyclin analogue in said subject at the end of the seventh day following administration is no less that $10^{-4}$, or $10^{-3}$, preferably no less than $10^{-2}$, more preferably no less than $10^{-1}$ times the plasma concentration of prostacyclin analogue in said subject at the end of the first day following administration (i.e. at 24 hours after administration).

In combination with the features and preferred features indicated herein, the method(s) of treatment of the present invention may have one or more of the following preferred features independently or in combination:

The method comprises the administration of at least one formulation with one or more preferred features as indicated above;

The method comprises the administration of at least one formulation as indicated herein by i.m., s.c. or preferably deep s.c. injection;

The method comprises administration by means of a pre-filled administration device as indicated herein;

The method comprises administration through a needle no larger than 20 gauge, preferably smaller than 20 gauge, and most preferably 23 gauge or smaller;

The method comprises a single administration every 3 to 10 days, preferably every 5 to 8 days.

The method comprises escalation of dose and frequency with progression of the disease (those indicated herein) such that the frequency escalates from no more than weekly to no less than on administration every 3 days and the dose escalates from no more than 10 or 20 mg/week to no less than 30 or 40 mg/week.

In combination with the features and preferred features indicated herein, the use(s) of the pre-formulations indicated herein in the manufacture of medicaments may have one or more of the following preferred features independently or in combination:

The use comprises the use of at least one formulation with one or more preferred features as indicated above;

The use comprises the manufacture of a medicament for administration of at least one formulation as indicated herein by i.m., s.c. or preferably deep s.c. injection;

The use comprises the manufacture of a medicament for administration by means of a pre-filled administration device as indicated herein;

The use comprises the manufacture of a medicament for administration through a needle no larger than 20 gauge, preferably smaller than 20 gauge, and most preferably 23 gauge or smaller;

The use comprises the manufacture of a medicament for administration daily, or once every 2, 3, 7, 14, 21, 28, 30, or 60 days and may be varied either systematically or occasionally by small amounts (e.g. by ±3 days, or by ±20% in any appropriate case).

In combination with the features and preferred features indicated herein, the pre-filled devices of the invention may have one or more of the following preferred features independently or in combination:

They contain a preferred formulation as indicated herein;

They comprise a needle smaller than 20 gauge, preferably no larger than 23 gauge;

They contain a single dose of at 2.5 to 50 mg/ml prostacyclin analogue (based on free acid), such as 5 to 50 mg/mL (based on free acid).

They contain a homogeneous mixture of a composition of the invention in ready-to-inject form.

They contain a formulation of components a) to c) for combination with a prostacyclin analogue whereby to form a pre-formulation of the invention.

They contain a total volume for administration of no more than 5 ml, preferably no more than 3 ml, for example no more than 2 ml, more preferably no more than 1.5 ml.

In combination with the features and preferred features indicated herein, the kits of the invention may have one or more of the following preferred features independently or in combination:

They contain a preferred formulation as indicated herein;

They contain a pre-filled device as indicated herein; They contain a needle smaller than 20 gauge, preferably no larger than 23 gauge;

They contain a single dose of 1 to 100 mg of a prostacyclin analogue (as described herein), preferably 2 to 75 mg, more preferably 3.5 to 60 mg.

They contain a "two compartment kit" comprising at least two vessels containing a lipid formulation of the invention and a prostacyclin analogue, respectively.

They contain a total volume for administration of no more than 5 ml, preferably no more than 3 ml, for example no more than 2 ml, more preferably no more than 1.5 ml.

They contain instructions for administration by a route and/or at a frequency as indicated herein;

They contain instructions for administration for use in a method of treatment as described herein.

As used herein, the term "about", "around", "substantially" or "approximately" in relation to a number or a range of numbers will generally indicate that the number or range specified is preferred but that such a number may be varied to a certain extend without materially affecting the properties of the relevant material, composition or similar product. The skilled worker will typically be able to readily establish the extent by which such numbers may be varied without prejudicing the key advantages of the present invention. As a general guide, such numbers or the ends of such ranges may be varied by ±10%, preferably ±5% and more preferably ±1%. A corresponding meaning may be attributed to compositions "consisting essentially of" certain components, which may include up to 10%, preferably up to 5% and most preferably up to 1% of other components in addition to those specified. Where a chemical group, chain or other moiety is described herein as optionally substituted, such substitution may be absent or one or more atoms in the moiety (typically one or more hydrogens and/or carbons) may be substituted with groups such as halide (e.g. F, Cl, Br, I) groups, oxygen-based moieties such as ethers, alcohols, esters carboxylic acids or epoxides, nitrogen-based groups such as amines, amides, nitriles or nitro groups, or sulphur-based groups such as thiols, disulphides, thioesters etc. Up to around 10 such substitutions may be made where context allows, but typically 3 or few substitutions, such as 1, 2 or 3 substitutions with independently selected substituent groups will be typical.

The Invention will now be further illustrated by reference to the following non-limiting Examples and the attached Figures.

EXAMPLES

Materials

Treprostinil sodium salt, TPN(Na), from Sanofi; soy phosphatidylcholine, SPC, Lipoid S100 from Lipoid; Glycerol dioleate, GDO, Cithrol GDO HP-SO-(LK) from Croda; dioleoyl phosphatidylcholine, DOPC, from NOF; Ethanol, EtOH (99.7% Ph. Eur), from Solveco; propylene glycol, PG (Ph. Eur), from Fischer; N-methyl pyrrolidone, NMP, and dimethylsulfoxide, DMSO, from Sigma-Aldrich were used as received. All other chemicals were of analytical grade purity.

Preparation of Pre-Formulations

Lipid stock mixtures were prepared by weighing appropriate amounts of SPC, GDO and solvents into sterilized glass vials. Sealed vials were then placed on a roller mixer at room temperature (RT) until mixed completely into clear homogeneous liquid solution (<24 hours). TPN(Na) powder was added to the respective lipid placebo formulations in new glass vials. Vials were then sealed and placed on a roller mixer at RT until mixed completely into clear homogeneous liquid solution (<24 hours). Prepared formulations were stored at RT in the dark until further experiments. For explorative stability evaluation, formulations were divided into sterilized 2R glass vials (1 g of formulation per vial). Vials were sealed and placed in controlled environment storage cabinets. At predefined sampling points two vials of formulation were withdrawn from each storage cabinet, placed at room temperature for 1 hour and analyzed for content and purity using gradient HPLC with UV detection.

Example 1: Evaluation of TPN(Na) Solubility and In Vitro Release

The solubility was assessed by adding TPN(Na) to respective lipid stock mixtures followed by mixing on a roller mixer at room temperature (RT) until mixed completely into clear homogeneous liquid solution. During preparation samples were visually inspected. Results showed that TPN (Na) has good solubility in a variety of pre-formulations and that a drug load of at least 7 wt % (~78 mg TPN(0)/mL) is feasible. As shown in Table 1, measured viscosities of the formulations range between 185-628 mPas depending on co-solvent type, concentration and composition.

TABLE 1

Viscosities of various pre-formulations containing 7 wt % TPN(Na).

| Formulation | Composition (wt %) | Viscosity (mPas) |
|---|---|---|
| A1 | TPN(Na)/GDO/SPC/EtOH 7.0/41.5/41.5/10.0 | 390 |
| A2 | TPN(Na)/GDO/SPC/EtOH/PG 7.0/41.5/41.5/5.0/5.0 | 628 |
| A3 | TPN(Na)/GDO/SPC/EtOH/PG 7.0/39.0/39.0/7.5/7.5 | 364 |
| A4 | TPN(Na)/GDO/SPC/EtOH/DMSO 7.0/39.0/39.0/7.5/7.5 | 305 |
| A5 | TPN(Na)/GDO/SPC/EtOH/DMSO 7.0/39.0/39.0/5.0/10.0 | 397 |
| A6 | TPN(Na)/GDO/SPC/EtOH/NMP 7.0/39.0/39.0/7.5/7.5 | 309 |
| A7 | TPN(Na)/GDO/SPC/EtOH/NMP 7.0/39.0/39.0/5.0/10.0 | 371 |
| A8 | TPN(Na)/GDO/SPC/EtOH 7.0/40.5/40.5/12.0 | 185 |
| A9 | TPN(Na)/GDO/DOPC/EtOH/PG 7.0/39.0/39.0/7.5/7.5 | 392 |

In vitro release testing of TPN(Na) was performed using a straightforward assay based on UV/VIS spectroscopy for quantification. In the test, depots were prepared by injecting 0.03-0.10 g (target 0.1 g) of the respective pre-formulation into 10 mL of PBS (pH 7.4) kept in 20R glass injection vials. The exact amount of formulation added to each vial was determined by weighing. The vials were sealed with rubber stoppers and aluminum crimp caps and placed on shaking in an incubator held at 37° C. Release media were sampled at scheduled time points, diluted and transferred to quartz cuvettes and analyzed on a Perkin Elmer Lambda 25, double-beam, UV-VIS spectrophotometer at 273 nm.

Figure 1B:
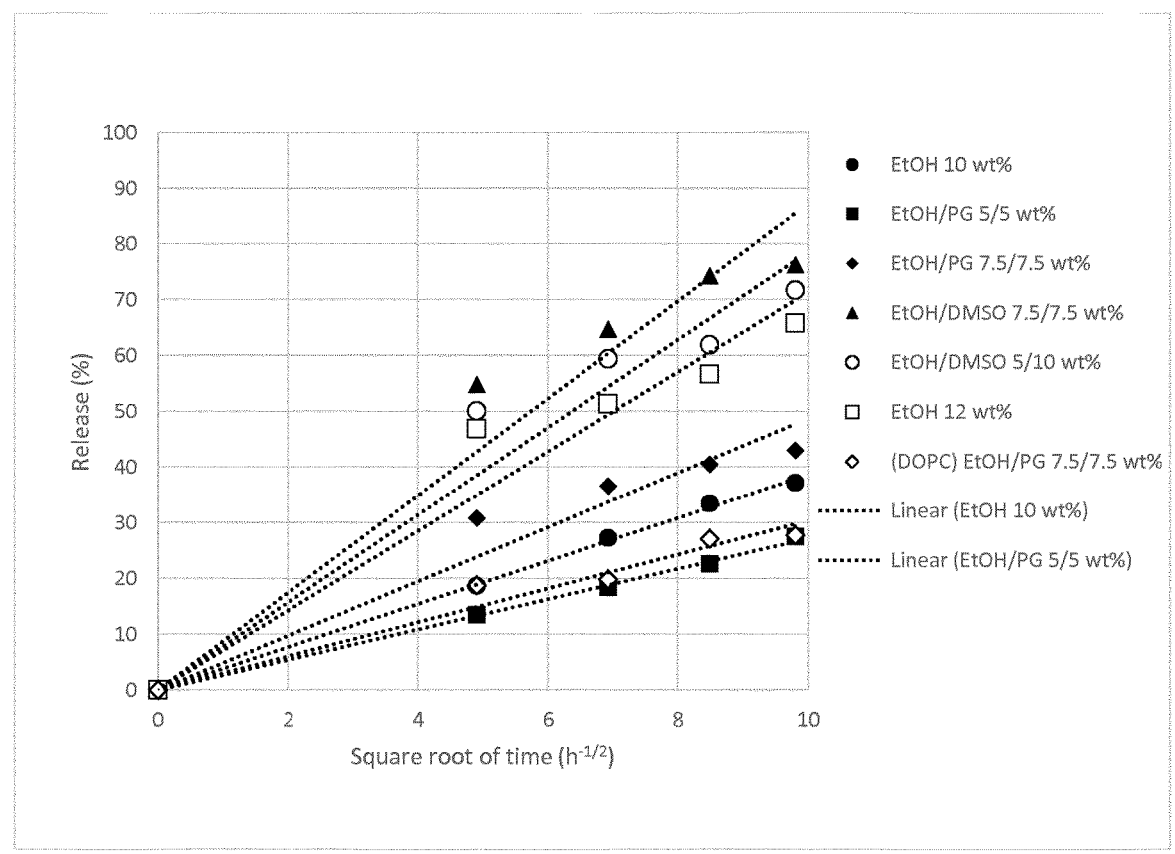

The results from the in vitro release measurements are displayed in FIG. 1a. From the results it is evident that both solvent amount and composition affect the initial in vitro release of treprostinil. Formulations comprising PG as co-solvent have a slower initial release (24 h) than formulations with DMSO. Also, when comparing formulations with EtOH as only solvent, the initial release is faster for higher solvent content. FIG. 1b further indicates that the release in vitro is biphasic, after the initial phase where solvent and drug is released concomitantly, the release is linear with square root of time as expected by a diffusion-controlled release mechanism from a monolithic depot matrix.

Example 2: Administration of Pre-Formulations with TPN(Na) in Rats: Formulations and Body Weight Change The primary objective of this pilot study was to evaluate the tolerability of TPN, both locally and systemically following single subcutaneous injections of pre-formulations with TPN(Na) to rats (formulation compositions are given in Table 2). The study was designed as a dose escalation study, with doses of administration of 3, 9 and 27 mg/kg TPN (Table 3).

TABLE 2

Formulation compositions used in the pilot rat study.

| Formulation | Composition (wt %) |
| --- | --- |
| B1 | TPN(Na)/GDO/SPC/EtOH/PG 3.1/43.45/43.45/5.0/5.0 |
| B2 | GDO/SPC/EtOH/PG 45.0/45.0/5.0/5.0 |

TABLE 3

Treatment groups and doses of TPN used in the pilot study.

| Treatment group | No. of animals | Formulation | Route of administration | Dose of TPN (mg/kg) | Dose volume (mL/kg) |
| --- | --- | --- | --- | --- | --- |
| 1 | 3 | B1 | s.c. | 3 | 0.11 |
| 2 | 3 | B1 | s.c. | 9 | 0.33 |
| 3 | 3 | B1 | s.c. | 27 | 1.00 |
| 4 | 3 | B2 | s.c. | — | 1.00 |

FIG. 2 shows the mean relative body weight change during the study. Formulations B1 and B2 were monitored in the pilot study for injection site erythema/edema as follows:

| Score | Classification |
| --- | --- |
| 0 | No erythema/edema |
| 1 | Slight erythema/edema (barely perceptible) |
| 2 | Modereate, well defined erythema/edema |
| 3 | Severa erythema to slight eschar formation/Severe edema |

The extent of erythema and edema formation following administration of formulations B1 and B2 is indicated in the Table 4 below:

TABLE 4

Summary of erythema and edema at the injection sites during the pilot study.

| Formulation | Animal No | 1 hr | 6 hrs | 1 day | 2 day | 5 day |
| --- | --- | --- | --- | --- | --- | --- |
| | | | Erythema | | | |
| B1 3 mg/kg | 1 | 0 | 0 | 0 | 1 | 0 |
| | 2 | 0 | 0 | 0 | 0 | 0 |
| | 3 | 0 | 0 | 0 | 0 | 0 |
| B1 9 mg/kg | 5 | 0 | 0 | 0 | 0 | 0 |
| | 6 | 0 | 0 | 0 | 0 | 0 |
| | 7 | 0 | 0 | 0 | 0 | 0 |
| B1 27 mg/kg | 9 | 0 | 0 | 0 | 0 | 0 |
| | 10 | 0 | 1 | 0 | 0 | 0 |
| | 11 | 0 | 0 | 0 | 0 | 0 |
| B2 | 4 | 0 | 0 | 0 | 0 | 0 |
| | 8 | 0 | 0 | 0 | 0 | 0 |
| | 12 | 0 | 0 | 0 | 0 | 0 |
| | | | Edema | | | |
| B1 3 mg/kg | 1 | 0 | 0 | 0 | 0 | 0 |
| | 2 | 0 | 0 | 2 | 1 | 1 |
| | 3 | 0 | 0 | 0 | 0 | 0 |
| B1 9 mg/kg | 5 | 0 | 0 | 0 | 0 | 0 |
| | 6 | 0 | 0 | 0 | 0 | 1 |
| | 7 | 0 | 0 | 0 | 0 | 0 |
| B1 27 mg/kg | 9 | 0 | 0 | 0 | 2 | 2 |
| | 10 | 0 | 0 | 0 | 2 | 2 |
| | 11 | 0 | 0 | 1 | 2 | 2 |
| B2 Placebo | 4 | 0 | 0 | 0 | 0 | 0 |
| | 8 | 0 | 0 | 0 | 0 | 0 |
| | 12 | 0 | 0 | 0 | 0 | 0 |

Formulations B1 and B2 were monitored in the pilot study for angiogenesis/haemorrhage as follows:

The level of angiogenesis was defined by a range from 0 to 3:

0 for no angiogenesis.

1 for minor angiogenesis. Limited growth of blood vessels.

2 for medium angiogenesis. Expanded growth of blood vessels 3 for major angiogenesis. Extensive growth of blood vessels.

The level of haemorrhage was defined by a range from 0 to 3:

0 for no haemorrhage.

1 for minor haemorrhage. Diffuse redness area or areas.

2 for medium haemorrhage. At least one well defined red area.

3 for major haemorrhage. Several well defined red areas.

The extent of angiogenesis and haemorrhage following administration of formulations B1 and B2 is indicated in Table 5 below.

TABLE 5

Summary of injection site findings at necropsy in the pilot study.

| Formulation | Animal No | Findings in the surrounding tissue | |
|---|---|---|---|
| | | Angiogenesis | Haemorrhage |
| B1 3 mg/kg | 1 | 2 | 1 |
| | 2 | 2 | 2 |
| | 3 | 2 | 0 |
| B1 9 mg/kg | 5 | 2 | 0 |
| | 6 | 3 | 3 |
| | 7 | 2 | 2 |
| B1 27 mg/kg | 9 | 3 | 2 |
| | 10 | 3 | 3 |
| | 11 | 3 | 3 |
| B2 | 4 | 0 | 0 |
| | 8 | 1 | 0 |
| | 12 | 1 | 0 |

Example 3: Effect on Nanostructure of the Fully Hydrated Pre-Formulations as a Function of Different Amounts of TPN(Na)

Formulations L to AA below were prepared which compositions and measured viscosities are given in Table 6 and FIG. 3, respectively.

TABLE 6

Formulation codes and compositions used for nanostructural evaluation.

| Formulation | SPC/GDO/EtOH (45:45:10) TPN(Na) (wt %) | SPC/GDO/EtOH/PG (42.5:42.5:7.5:7.5) TPN(Na) (wt %) |
|---|---|---|
| L | 0.00 | — |
| M | 0.78 | — |
| N | 1.53 | — |
| O | 2.33 | — |
| P | 3.13 | — |
| Q | 4.66 | — |
| R | 6.17 | — |
| S | 7.76 | — |
| T | — | 0.00 |
| U | — | 0.77 |
| V | — | 1.55 |
| W | — | 2.33 |
| X | — | 3.07 |
| Y | — | 4.63 |
| Z | — | 6.14 |
| AA | — | 7.74 |

The nanostructure of the fully hydrated formulations from Table 6 was evaluated using small angle X-ray diffraction. Briefly, about 100 mg of the formulation was injected into 5 mL PBS buffer and left to equilibrate at ambient RT in still standing vials for 8 days before SAXD measurements. The nanostructure of fully hydrated formulations as a function of TPN(Na) concentration was studied using synchrotron SAXD measurements, performed at the 1911-4 beamline at MAX IV laboratory (Max II electron accelerator operating at 1.5 GeV, Lund University, Sweden), using a 1M PILATUS 2D detector (Dectris) containing a total of 981×1043 pixels. Samples were mounted between thin polyimide films in a custom made steel sample holder at the sample to detector distance of 1919.5 mm. Diffractograms were recorded with a X-ray wavelength of 0.91 Å and the beam cross-section of 0.25×0.25 mm (full width at the half-maximum) at the sample. Temperature control was achieved using computer controlled Lauda RE 420G thermostat (Lauda-Brinkmann, LP). The experiments were performed successively at 25, 37, and 42° C. with a 60 s exposure time at each temperature and a wait of 10 minutes between temperature steps. The resulting CCD images were integrated and analyzed using the Fit2D software provided by ESRF (European Synchrotron Radiation Facility, France). Silver behenate calibrated sample-to-detector distance and detector positions were used.

FIG. 5 and FIG. 6 show obtained SAXD results of the nanostructure of the fully hydrated Lipid/EtOH (90/10 wt %) and Lipid/EtOH/PG (85/7.5/7.5) formulations as a function of TPN concentration and temperature. Data in FIG. 5 show that in the temperature region of 37-42° C. fully hydrated 10% EtOH based formulations form mixtures of reversed hexagonal (H2) and reversed micellar cubic (Fd3m) phases up to 3.1 wt % of TPN. At 4.65 and 6.2 wt % of TPN a single H2 is formed which at even higher concentrations of TPN starts to transform into disordered micellar solution (L2). In addition, with increasing TPN concentration the lattice parameter for Fd3m phase remains unchanged whereas it starts to increase for the H2 phase. The increase of the lattice parameter starting from 4.65 wt % of TPN(Na) is likely related to the increased mechanical softness of the depots observed in gelling experiments. Overall, the observed transformation from mixture of Fd3m and H2 to single H2 and further to a mixture of H2 and L2 phases with increasing concentration of TNP correlates with the obtained in vitro release results where drastic increase in released TPN is found at 6.2 and 7.75 wt % of TPN (FIG. 4). As a comparison, FIG. 6 shows SAXD results obtained for the fully hydrated formulations prepared at 7.5/7.5 wt % of EtOH/PG mixture. Here, in the temperature region of 37-42° C., clearly pronounced mixture of Fd3m and H2 phases is formed only up to 1.55 wt % of TPN. With increasing TPN concentration between 2.33 and 6.2 wt % of TPN an H2 phase mixture with L2 phase is observed. Furthermore, at 7.75 wt % of TPN a mixture of lamellar (Lα) and L2 phase is formed. In addition, the lattice parameter for the hexagonal phase starts to increase already at 3.10 wt % of TPN(Na). Based on these results, it may be concluded that fully hydrated formulations prepared using EtOH/PG 7.5/7.5 can accommodate less of TPN before transforming into more swollen liquid crystalline phases (especially Lα) which are less favourable from the perspective of sustained release.

Figure 4B:
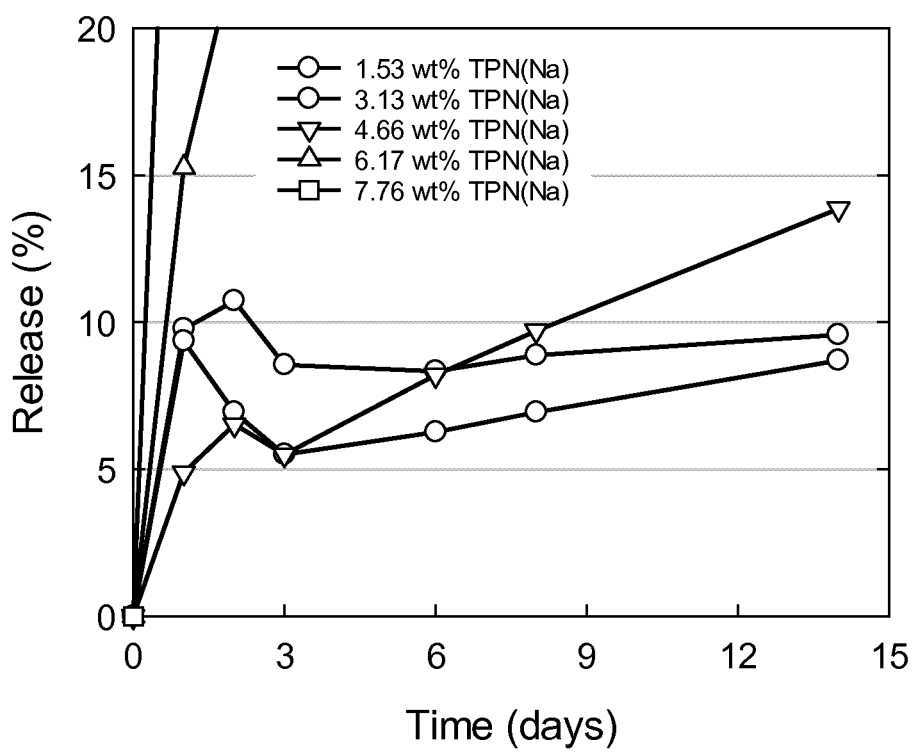

In-vitro release profiles for formulations N, P, Q, R and S were measured and are shown in FIGS. 4a-b (cumulative % release).

Example 4: Physical and Chemical Stability of Pre-Formulations Containing TPN(Na)

The storage stability of formulations BB, CC and DD (Table 7 and 8) was studied by HPLC under conditions of: ≤−25° C. (frozen conditions); 25° C./60% RH; and 40° C./75% RH. Results from the explorative stability testing indicate good physical as well as chemical stability of TPN in the pre-formulations using both 10% EtOH as solvent and with a mixture of EtOH/PG. TPN shows good stability for at least up to 3 months when stored at 25° C./60% RH and 40° C./75% RH (Table 9).

TABLE 7

Formulation codes and compositions used for physical and chemical stability evaluation.

| Formulation | TPN(Na)/SPC/GDO/EtOH/PG (wt %) |
|---|---|
| BB | 2.78/43.61/43.61/5.0/5.0 |
| CC | 2.78/43.61/43.61/10.0/0 |
| DD | 1.39/44.31/44.31/10.0/0 |

TABLE 8

Formulation codes and viscosities used for physical and chemical stability evaluation.

| Formulation | Time zero (mPas) | 1.5 months (mPas) | 3 months (mPas) | Storage conditions |
|---|---|---|---|---|
| BB | 544 | 582 | 562 | ≤−25° C. |
| CC | — | 278 | — | ≤−25° C. |
| BB | 544 | 586 | 566 | 25° C., 60% RH |
| CC | — | 300 | — | 25° C., 60% RH |
| BB | 544 | 589 | 561 | 40° C., 75% RH |
| CC | — | 296 | — | 40° C., 75% RH |
| DD | — | 257 | — | 40° C., 75% RH |

TABLE 9

TPN assay results (HPLC) in the formulations from the explorative stability study as a function of time at different storage conditions.

| Sample ID and storage | Target conc. mg/g | Solvent | Time zero % of target | 1.5 months % of target | 3 months % of target |
|---|---|---|---|---|---|
| BB, ≤−25° C. | 27.8 | EtOH/PG 5/5 wt % | 99 | 103 | 101 |
| CC, ≤−25° C. | 27.8 | EtOH 10 wt % | 100 | 100 | 97 |

| Sample ID | Conc. mg/g | Solvent | Time zero % of target | 1.5 months % of target | 3 months % of target |
|---|---|---|---|---|---|
| BB, 25° C./60% RH | 27.8 | EtOH/PG 5/5 wt % | 99 | 102 | 100 |
| CC, 25° C./60% RH | 27.8 | EtOH 10 wt % | 100 | 102 | 99 |
| BB, 40° C./75% RH | 27.8 | EtOH/PG 5/5 wt % | 99 | 101 | 100 |
| CC, 40° C./75% RH | 27.8 | EtOH 10 wt % | 100 | 100 | 98 |
| DD, 40° C./75% RH | 13.9 | EtOH 10 wt % | 100 | 101 | Not tested |

Example 5: Administration of Pre-Formulations with TPN(Na) in Rats

Formulations EE-HH were prepared using different solvent compositions (Table 10) and were administered to a group of 24 rats and monitored for Erythema, Edema Angiogenesis and Haemorrhage using the scoring system of earlier Examples.

TABLE 10

Formulation compositions and TPN doses used in the rat PK study

| Formulation | Composition (wt %) | Dose of TPN (mg/kg) | Dose volume (mL/kg) |
|---|---|---|---|
| EE | TPN(Na)/GDO/SPC/EtOH/PG 3.10/43.45/43.45/5.0/5.0 | 9.0 | 0.33 |
| FF | TPN(Na)/GDO/SPC/EtOH 3.10/43.45/43.45/10.0 | 9.0 | 0.33 |
| GG | TPN(Na)/GDO/SPC/EtOH 1.55/44.23/44.23/10.0 | 4.5 | 0.33 |
| HH | TPN(Na)/GDO/SPC/EtOH/DMSO 3.10/43.45/43.45/5.0/5.0 | 18 | 0.66 |

TABLE 11

Extent of erythema following administration of Formulations EE-HH.

| Test Item | Treatment group | Animal no | Erythema | | | | | | | |
|---|---|---|---|---|---|---|---|---|---|---|
| | | | 1 hr | 6 hrs | 1 day | 2 day | 5 day | 8 day | 14 day | 28 day |
| EE | 1A | Rat 01 | 0 | 0 | 0 | 0 | 0 | 0 | 0 | NA |
| | | Rat 09 | 0 | 0 | 0 | 0 | 1* | 0 | 0 | NA |
| | | Rat 17 | 0 | 0 | 0 | 0 | 0 | 0 | 0 | NA |
| | 1B | Rat 08 | 0 | 0 | 0 | 0 | 0 | 1 | 0 | 0 |
| | | Rat 16 | 0 | 0 | 0 | 0 | 0 | 0 | 0 | 0 |
| | | Rat 24 | 0 | 0 | 0 | 0 | 0 | 0 | 0 | 0 |
| FF | 2A | Rat 02 | 0 | 0 | 0 | 1 | 0 | 0 | 0 | NA |
| | | Rat 10 | 0 | 0 | 0 | 0 | 0 | 0 | 0 | NA |
| | | Rat 18 | 0 | 0 | 0 | 0 | 0 | 0 | 0 | NA |
| | 2B | Rat 07 | 0 | 0 | 0 | 0 | 0 | 0 | 0 | 0 |
| | | Rat 15 | 0 | 0 | 0 | 1 | 0 | 0 | 0 | 0 |
| | | Rat 23 | 0 | 0 | 0 | 1* | 0 | 0 | 0 | 0 |
| GG | 3A | Rat 03 | 0 | 0 | 0 | 0 | 0 | 0 | 0 | NA |
| | | Rat 11 | 0 | 0 | 0 | 0 | 0 | 0 | 0 | NA |
| | | Rat 19 | 0 | 0 | 0 | 0 | 0 | 0 | 0 | NA |
| | 3B | Rat 06 | 0 | 0 | 0 | 0 | 0 | 0 | 0 | 0 |
| | | Rat 14 | 0 | 0 | 0 | 1* | 0 | 0 | 0 | 0 |
| | | Rat 22 | 0 | 0 | 0 | 0 | 0 | 0 | 0 | 0 |
| HH | 4A | Rat 04 | 0 | 0 | 0 | 0 | 0 | 0 | 0 | NA |
| | | Rat 12 | 0 | 0 | 0 | 0 | 1* | 0 | 0 | NA |
| | | Rat 20 | 0 | 0 | 0 | 0 | 0 | 0 | 0 | NA |
| | 4B | Rat 05 | 0 | 0 | 0 | 0 | 0 | 0 | 0 | 0 |
| | | Rat 13 | 0 | 0 | 0 | 0 | 0 | 0 | 0 | 0 |
| | | Rat 21 | 0 | 0 | 0 | 0 | 0 | 0 | 0 | 0 |

TABLE 12

Extent of edema following administration of Formulations EE-HH.

| Test Item | Treatment group | Animal no | Edema* | | | | | | | |
|---|---|---|---|---|---|---|---|---|---|---|
| | | | 1 hr | 6 hrs | 1 day | 2 day | 5 day | 8 day | 14 day | 28 day |
| EE | 1A | Rat 01 | 0 | 0 | 0 | 0 | 0 | 0 | 0 | NA |
| | | Rat 09 | 0 | 0 | 0 | 0 | 0 | 0 | 0 | NA |
| | | Rat 17 | 0 | 0 | 1 | 0 | 0 | 0 | 0 | NA |
| | 1B | Rat 08 | 0 | 0 | 1 | 0 | 0 | 0 | 0 | 0 |
| | | Rat 16 | 0 | 0 | 1 | 1 | 1 | 0 | 0 | 0 |
| | | Rat 24 | 0 | 0 | 0 | 0 | 0 | 0 | 0 | 0 |
| FF | 2A | Rat 02 | 0 | 0 | 0 | 0 | 0 | 0 | 0 | NA |
| | | Rat 10 | 0 | 0 | 1 | 1 | 1 | 0 | 0 | NA |
| | | Rat 18 | 0 | 0 | 0 | 0 | 0 | 0 | 0 | NA |
| | 2B | Rat 07 | 0 | 0 | 1 | 0 | 0 | 0 | 0 | 0 |
| | | Rat 15 | 0 | 0 | 0 | 0 | 0 | 0 | 0 | 0 |
| | | Rat 23 | 0 | 0 | 0 | 0 | 1 | 1 | 0 | 0 |
| GG | 3A | Rat 03 | 0 | 0 | 1 | 0 | 0 | 0 | 0 | NA |
| | | Rat 11 | 0 | 0 | 1 | 0 | 0 | 0 | 0 | NA |
| | | Rat 19 | 0 | 0 | 1 | 0 | 0 | 0 | 0 | NA |
| | 3B | Rat 06 | 0 | 1 | 0 | 0 | 0 | 0 | 0 | 0 |
| | | Rat 14 | 0 | 0 | 0 | 0 | 0 | 0 | 0 | 0 |
| | | Rat 22 | 0 | 0 | 1 | 0 | 0 | 0 | 0 | 0 |
| HH | 4A | Rat 04 | 0 | 0 | 0 | 0 | 0 | 0 | 0 | NA |
| | | Rat 12 | 0 | 0 | 1 | 0 | 0 | 0 | 0 | NA |
| | | Rat 20 | 0 | 0 | 0 | 0 | 0 | 0 | 0 | NA |
| | 4B | Rat 05 | 0 | 1 | 0 | 0 | 0 | 0 | 0 | 0 |
| | | Rat 13 | 0 | 0 | 1 | 1 | 1 | 0 | 0 | 0 |
| | | Rat 21 | 0 | 0 | 0 | 0 | 0 | 0 | 0 | 0 |

TABLE 13

Injection site at necropsy following administration of Formulations EE-HH.

| Test Item | Treatment group | Animal no | Angiogenesis[1] | Hemorrhage[2] | No of depot remains |
|---|---|---|---|---|---|
| EE | 1A | Rat 01 | 1 | 0 | 2 |
|  |  | Rat 09 | 2 | 0 | 2 |
|  |  | Rat 17 | 2 | 0 | 1 |
|  | 1B | Rat 08 | 2 | 0 | 2 |
|  |  | Rat 16 | 1 | 0 | 1 |
|  |  | Rat 24 | 2 | 0 | 1 |
| FF | 2A | Rat 02 | 1 (+) | 0 | 4 |
|  |  | Rat 10 | 2 | 0 | 2 |
|  |  | Rat 18 | 2 | 0 | 2 |
|  | 2B | Rat 07 | 2 | 0 | 1 |
|  |  | Rat 15 | 1 | 0 | 1 |
|  |  | Rat 23 | 1 | 0 | * |
| GG | 3A | Rat 03 | 2 | 0 | 2 |
|  |  | Rat 11 | 2 | 0 | 3 |
|  |  | Rat 19 | 1 | 0 | 3 |
|  | 3B | Rat 06 | 2 | 0 | 2 |
|  |  | Rat 14 | 2 | 0 | 1 |
|  |  | Rat 22 | 2 | 0 | 1 |
| HH | 4A | Rat 04 | 2 | 0 | 4 |
|  |  | Rat 12 | 1 | 0 | 1 |
|  |  | Rat 20 | 1 | 0 | 3 |
|  | 4B | Rat 05 | 2 | 0 | 1 |
|  |  | Rat 13 | 1 | 0 | 2 |
|  |  | Rat 21 | 2 | 0 | 2 |

Example 6: Rat PK Data of Pre-Formulations with TPN(Na)

Pharmacokinetic data was collected over 14 days for formulations EE to HH of Example 7 administered to rats. The data is illustrated graphically in FIG. 7 and the corresponding in vitro release profiles in FIG. 8.

TABLE 14

PK parameters for Formulations EE-HH in rats. The data is illustrated graphically in FIG. 10 and percentage release profile in FIG. 11.

| Test Item | Value | $C_{max}$ (ng/mL) | $C_{max}$ ((ng/mL)/ (mg/kg)) | $t_{max}$ (days) | $AUC_{last}$ (ng/mL*d) | $AUC_{last}$ ((ng/mL*d)/ (mg/kg)) | $AUC_{24h}/AUC_{last}$ (%) |
|---|---|---|---|---|---|---|---|
| EE | Mean | 41.6 | 4.52 | 0.042 | 104 | 11.4 | 20.9 |
|  | SD | 11.4 | 1.15 | — | 18.0 | 1.90 | 6.27 |
| FF | Mean | 43.1 | 4.79 | 0.042 | 108 | 12.1 | 23.9 |
|  | SD | 11.7 | 1.25 | — | 12.9 | 1.33 | 7.59 |
| GG | Mean | 27.4 | 6.00 | 0.042 | 48.0 | 10.5 | 24.6 |
|  | SD | 4.44 | 1.01 | — | 12.3 | 2.80 | 3.49 |
| HH | Mean | 57.4 | 3.26 | 0.042 | 160 | 9.16 | 21.1 |
|  | SD | 11.1 | 0.64 | — | 90.7 | 5.31 | 5.41 |

Example 7: Subcutaneous Injection of Pre-Formulations with TPN(Na) in Dogs

The objective of this study was to assess the exposure to TPN following subcutaneous injection of the pre-formulation with TPN(Na) (formulation code JJ, composition TPN(Na)/GDO/SPC/EtOH/PG 3.38/43.31/43.31/70.50/2.50 wt %) to beagle dogs in a maximum tolerated dose toxicity study. The TPN doses (calculated as TPN acid form) used in the dog study are given in Table 15. The obtained dose dependent PK profiles and exposure (AUC0-168 h) values are presented in FIG. 9 and FIG. 10, respectively.

TABLE 15

TPN dose levels and volumes used in the dog PK study.

| Formulation | Dose level (mg/dose) | Dose volume (mL) |
|---|---|---|
| JJ | 3 | 0.1 |
|  | 15 | 0.5 |
|  | 22.5 | 0.75 |
|  | 30 | 1.0 |

The invention claimed is:
1. A pre-formulation comprising:
a) 38 to 52 wt % of at least one of a mono-, di- or tri-acyl lipid and/or a tocopherol;
b) 35 to 55 wt % of at least one phospholipid;

c) 1 to 30 wt % of at least one biocompatible, organic solvent; and
d) 0.1 to 6.2% of treprostinil (TPN) or a salt thereof, based on the TPN free acid;
wherein the pre-formulation forms, or is capable of forming, at least one liquid crystalline phase structure upon contact with excess aqueous fluid,
wherein the pre-formulation is a molecular solution,
wherein component c) comprises ethanol or mixtures of ethanol and propylene glycol (PG), wherein the ratio of ethanol to PG is 1:1 to 10:1, and wherein component c) is present at a level of 2 to 20% by weight.

2. A pre-formulation of claim 1 comprising 0.1 to 4% of component d) based on the TPN free acid.

3. A pre-formulation of claim 1 wherein component a) comprises a neutral diacyl and/or monoacyl lipid.

4. A pre-formulation of claim 1 wherein component a) comprises a diacyl glycerol.

5. A pre-formulation of claim 1 comprising 41 to 45 wt % component a).

6. A pre-formulation of claim 1 wherein component b) comprises a phosphatidyl choline (PC).

7. A pre-formulation of claim 1 comprising 41 to 45 wt % component b).

8. A pre-formulation of claim 1 wherein component c) further comprises at least one solvent selected from the group consisting of: alcohols, amines, amides, sulphoxides esters, and mixtures thereof.

9. A pre-formulation of claim 1 wherein component c) comprises ethanol.

10. A pre-formulation of claim 1 wherein component c) further comprises a mono-alcoholic solvent and a sulphoxide or an amide.

11. A pre-formulation of claim 1 wherein component c) is present at a level of 5 to 15% by weight.

12. A pre-formulation of claim 1 wherein the ratio of components a:b is in the range of 40:60 to 60:40.

13. A pre-formulation of claim 1 wherein:
component a) comprises soy phosphatidylcholine (PC);
component b) comprises glycerol dioleate (GDO);
component c) comprises ethanol; and
component d) comprises treprostinil sodium (TPN(Na)) or a salt thereof.

14. A pre-formulation of claim 13 further comprising a co-solvent selected from the group consisting of propylene glycol (PG), dimethylsulphoxide (DMSO), and N-methyl-pyrrolidone (NMP), wherein the ratio of ethanol:co-solvent is in the range of 30:70 to 70:30 (w/w).

15. A method of sustained administration of treprostinil (TPN) to a human or non-human mammalian subject, comprising administering to said subject a pre-formulation of claim 1.

16. A medicament comprising the pre-formulation of claim 1.

17. A method for the treatment of a human or non-human mammalian subject comprising administering to said subject a pre-formulation of claim 1.

18. The method of claim 17 for the treatment of a human or non-human mammalian subject in need thereof to treat at least one condition selected from pulmonary artery hypertension (PAH), severe PAH, Raynaud's disease, and ischemia.

19. The medicament of claim 16 for use in the in vivo formation of a depot for treatment of at least one condition selected from pulmonary artery hypertension (PAH), severe PAH, Raynaud's disease, and ischemia.

20. A pre-filled administration device containing a pre-formulation of claim 1.

21. A kit comprising an administration device of claim 20.

22. A pre-formulation of claim 1 comprising 0.5 to 4% of component d) based on the TPN free acid.

23. The method of claim 17, wherein the administration route is not intravenous, or is shallow or deep subcutaneous injection, topical, or intraoral.

24. The method of claim 17, wherein administration occurs every 1 to 60 days.

25. The method of claim 17, wherein the administration occurs every 1, 2, 3, 7, 14, 21, 28, 30, or 60 days.

26. The method of claim 17, wherein the administration occurs every 7 (±1) days, every 14 (±2) days, or every 30 (±3) days.

27. The method of claim 17, wherein the administration occurs every 7 (±1) days.

28. The pre-filled administration device of claim 20, comprising 1 mL of the pre-formulation.

29. A pre-formulation of claim 1, wherein component c) comprises mixtures of ethanol and PG, wherein the ratio of ethanol to PG is 1:1 to 10:1.

30. A pre-formulation of claim 1, wherein component c) comprises mixtures of ethanol and PG, wherein the ratio of ethanol to PG is 1.5:1 to 8:1.

31. A pre-formulation of claim 1, wherein component c) comprises mixtures of ethanol and PG, wherein the ratio of ethanol to PG is 2:1 to 5:1.

* * * * *